United States Patent [19]

Hirschman et al.

[11] Patent Number: 4,854,324

[45] Date of Patent: Aug. 8, 1989

[54] PROCESSOR-CONTROLLED ANGIOGRAPHIC INJECTOR DEVICE

[75] Inventors: Alan D. Hirschman; David M. Reilly, both of Glenshaw; Ross H. Potter, Oakmont; John Stulen, Pittsburgh; Eric M. Toft, Pittsburgh; John G. Clark, Pittsburgh, all of Pa.

[73] Assignee: Medrad, Inc., Pittsburgh, Pa.

[21] Appl. No.: 161,434

[22] Filed: Feb. 24, 1988

Related U.S. Application Data

[63] Continuation of Ser. No. 575,591, Jan. 31, 1984, abandoned.

[51] Int. Cl.[4] ............................................. A61M 37/00
[52] U.S. Cl. .............................. 128/655; 128/DIG. 1; 604/67; 604/155
[58] Field of Search ................................ 128/655–658, 128/DIG. 1, DIG. 12, DIG. 13; 604/67, 154, 155, 245

[56] References Cited

U.S. PATENT DOCUMENTS

| | | | |
|---|---|---|---|
| 2,432,605 | 12/1947 | Barach | 604/207 |
| 3,701,345 | 10/1972 | Heilman et al. | 128/655 |
| 3,812,843 | 5/1974 | Wooten et al. | 604/155 |
| 4,006,736 | 2/1977 | Kranys et al. | 128/DIG. 1 X |
| 4,221,543 | 9/1980 | Cosentino et al. | 128/DIG. 12 X |
| 4,232,679 | 11/1980 | Schulman | 128/419 PG |
| 4,308,866 | 1/1982 | Jelliffe et al. | 604/31 |
| 4,465,474 | 8/1984 | Mardorf et al. | 604/154 |
| 4,469,481 | 9/1984 | Kobayashi | 128/DIG. 1 X |
| 4,475,666 | 10/1984 | Bilbrey | 604/155 X |
| 4,529,401 | 7/1985 | Leslie et al. | 128/DIG. 1 X |
| 4,559,037 | 12/1985 | Franetzki et al. | 604/891 X |
| 4,685,903 | 8/1987 | Cable et al. | 604/154 |

OTHER PUBLICATIONS

Lowe, H. J., "Dose-Regulated Penthane Anesthesia", Data Trak ®, 1972, pp. 99–109.
"IMED Computer Controlled Infusion Pump Model 979" Amer. Hrt. Assn. Meetings, Dallas, 11/13–11/16/1978.
Crane, J. et al, "A Programmable Infusion Pump", presented at 30th ACEMB Conf., 11-5/11-9-77, L.A., Calif.

Primary Examiner—Francis Jaworski
Attorney, Agent, or Firm—Fleit, Jacobson, Cohn & Price

[57] ABSTRACT

An angiographic injector device for use in x-ray photography for delivering contrast media to a patient at controlled rates and pressures. A processor elicits injection parameters from an operator or a pre-programmed injection module, and on the basis of the injection parameters, calculates appropriate control signals for use in a closed-loop servo system to actuate the plunger of a syringe containing the contrast media. Injection parameters includes flow rate, volume, duration, pressure limit and rise-fall time of flow rate. The device also includes control circuits for inhibiting the injection device in response to a contrast media pressure limit, failure in the processor or injection control system, or upon reaching a predetermined volume of injected media. A mechanical stop member cooperates with the control circuit for blocking movement of the syringe plunger upon reaching the predetermined injected volume. Further, the device includes a self-test feature for checking the status of operational components thereof and a self-calibration feature for calibrating the servo system and position monitors. To improve reliability and to provide immunity from data corruption due to line power interruption, injection parameters are stored in battery-powered primary and secondary memories, and are compared and verified prior to an injection. To assist in coordinating an injection in synchronism with cardiac activity, the device monitors the ECG waveform of the patient's heart and injects a small bolus of contrast media at a given interval, such as the distolic interval. An interface also is provided for providing remote transfer of status and control information with the angiographic injector device.

37 Claims, 14 Drawing Sheets

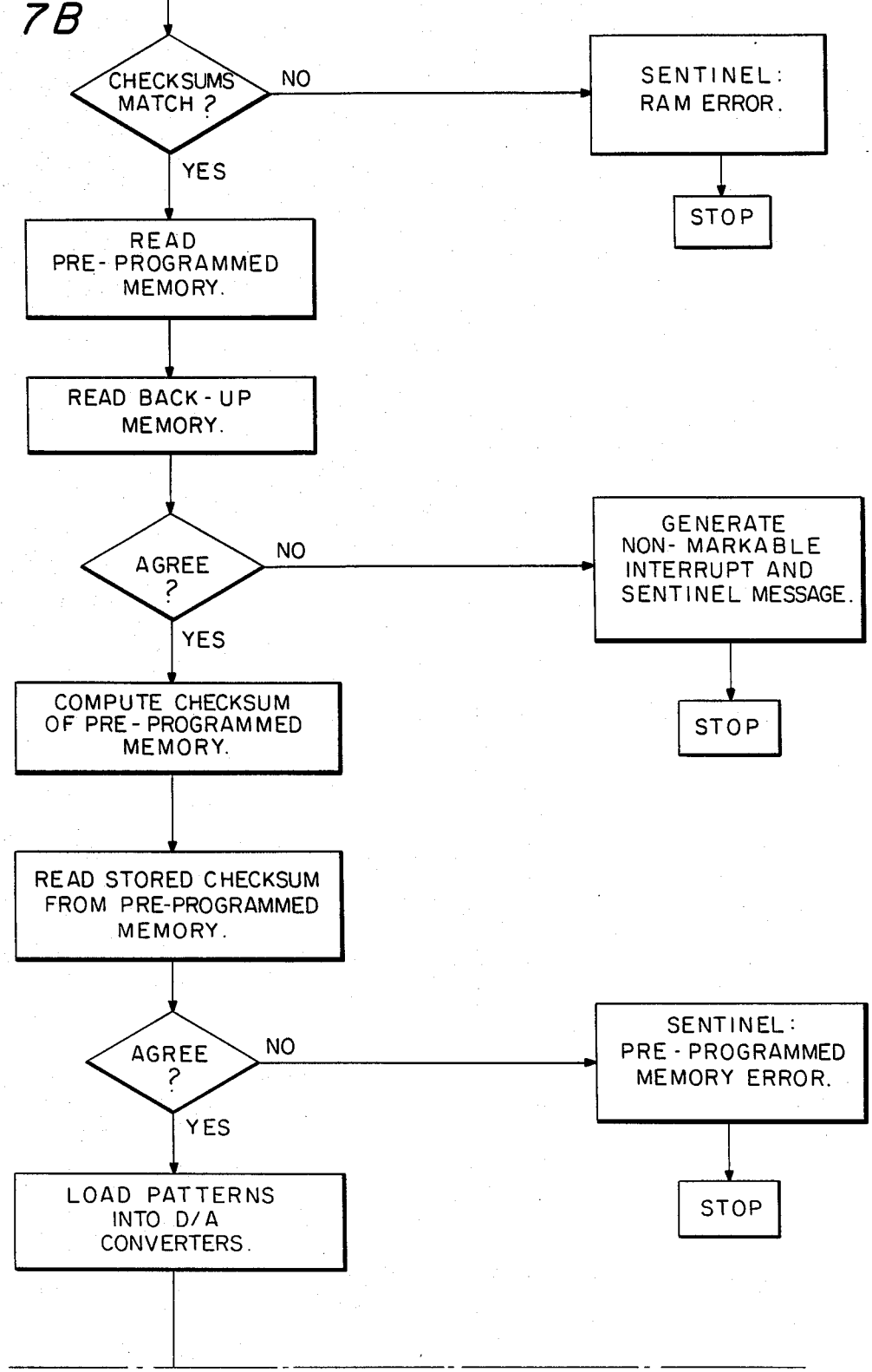

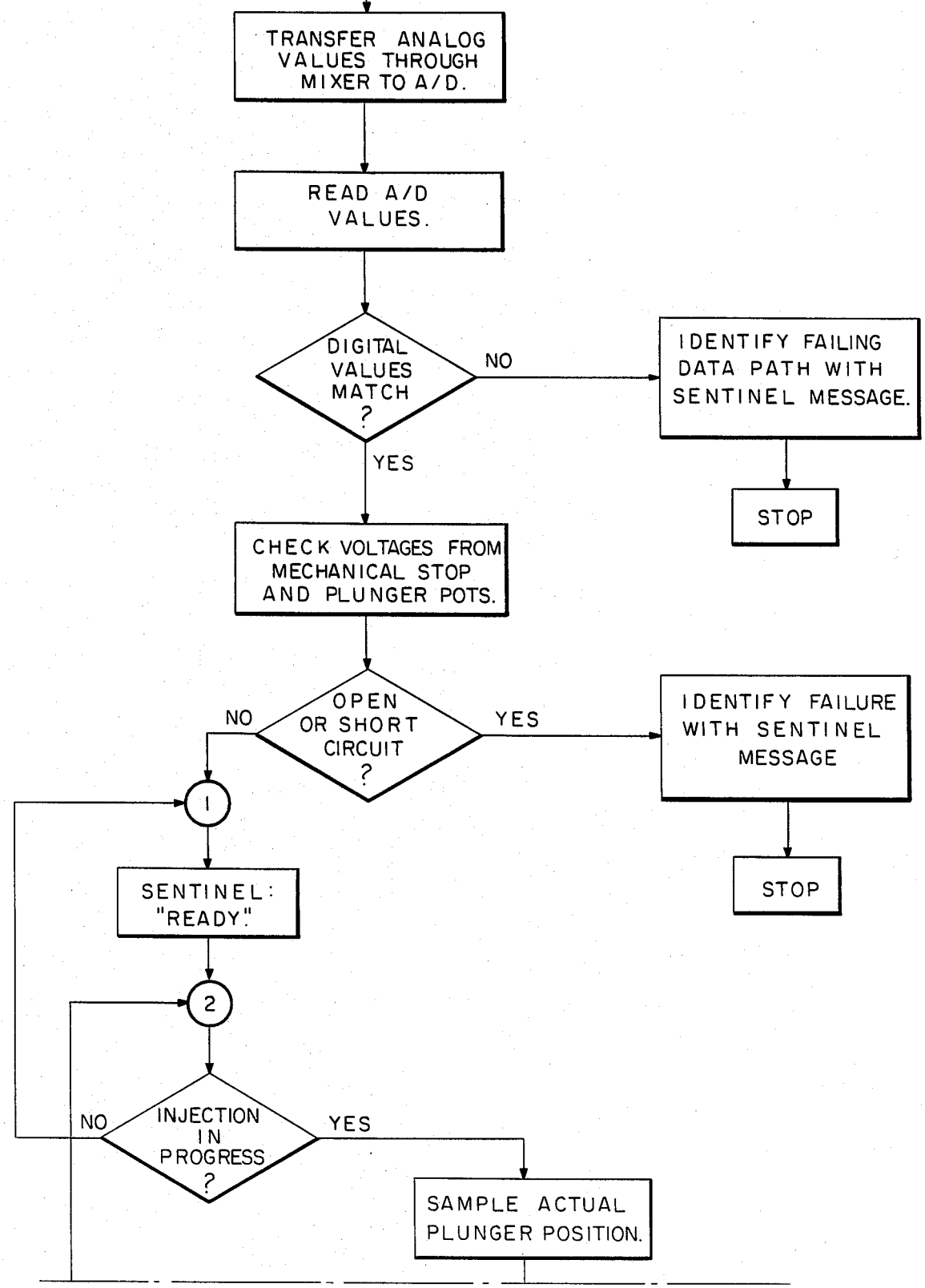

PROCESSOR-CONTROLLED ANGIOGRAPHIC INJECTOR DEVICE

This application is a continuation of application Ser. No. 575,591, filed Jan. 31, 1984 and now abandoned.

BACKGROUND OF THE INVENTION

This invention pertains to angiographic devices for injecting into a patient contrast media at a controlled rate and pressure during x-ray photography. More specifically, this invention is an improvement over commonly assigned, incorporated U.S. Pat. No. 4,006,736, which improvement concerns automated control of such angiographic injector devices being responsive to input information supplied by an operator to develop control signals for automatically controlling the injection process.

An angiographic injector is useful for controlling the delivery rate, amount, duration, and pressure of contrast media, usually a liquid iodine solution, injected into a patient. Such devices are used in x-ray photography to enhance the contrast of the image obtained thereby. In a typical operation of such device, an operator loads the same with a certain amount of contrast media, connects a delivery tube extending from a fluid reservoir of the device to a catheter placed in the vascular system of a patient, and then actuates the device by forcing the media into the blood stream while exposing the patient to x-rays during the photographic process. Among other things, it is very important that the proper amount of contrast media, as well as the pressure and rate at which it is delivered, be controlled accurately for safe and desirable results.

One such angiographic injector device over which the present invention is an improvement is described in U.S. Pat. No. 4,006,736 issued to Kranys et al, commonly owned by the assignee hereof. As with many other types of angiographic injector devices, this system is rather mechanical and although efficient, does not take advantage of certain potential automatic control and test features which can facilitate its use and reduce the likelihood of errors during its operation. As known, certain errors can be fatal or expose the patient to undue risks of harm.

As examples of potential capabilities under automated control, it is often desirable to provide multi-level injections during an x-ray photographing sequence. In this case, the contrast media is injected, for example, in step-wise changing flow rates and/or pressures. It is also desirable to provide multiphasic injections in which the programmed injection profile is delivered several times in succession under operator or remote control. Also, it may be desirable to automatically compute parameters involved in the injection of a specific amount of contrast media and to enable the size of the syringe to be changed without adversely affecting the operation of the injection and without requiring reprogramming. Such features are not known to exist with prior art devices. Moreover, certain mechanical control and electronic control features can be integrated to enhance reliability, such as by providing a mechanical stop member to prevent further movement of a syringe plunger when a predetermined amount of contrast media already has been injected. Additionally, rather than requiring the operator to calculate flow rates and/or volumes, this can automatically be computed by a processor controlled system as a function of an injection parameter supplied to the system by the operator, whereupon the system itself would then calculate the corresponding pressure and control signals for delivery of the media. Still further, the use of a microprocessor in an angiographic injector device enables various programming verification steps not otherwise available. These are only a few automatic control features which are not known to exist with prior art systems.

In view of the foregoing, it is a primary objective of the present invention to provide a processor-controlled angiographic injector device for automatically delivering contrast media at controlled rates, pressures or volumes, which rates and pressures or volumes are automatically calculated on the basis of injection parameters supplied thereto by a user.

It is an additional objective of the present invention to provide safety and/or control features which limit the injection pressure and/or delivery of contrast media when certain limits are exceeded, such as a pressure limit of contrast media in the syringe.

It is yet a further objective of the present invention to provide a mechanical stop mechanism for mechanically preventing the plunger of a syringe from further movement when a given amount of contrast media has been injected, wherein the stop position is automatically determined on the basis of injection information supplied to the device.

It is an additional objective of the present invention to interlock the operation of the mechanical stop mechanism and a plunger drive circuit of the injector device so that they alternate in operation to ensure that the drive circuit of the plunger does not operate until the drive circuit of the stop mechanism has completed its setting of the stop position.

Another objective of the present invention is to provide a multi-level injection sequence under processor control whereby the duration and/or injection rate and/or pressure may step-wise be changed during separate injection sequences, as well as to provide means for compensating the plunger drive rate and delivered pressure on the basis of syringe size during the injection process.

An additional objective of the present invention is to provide pre-programmed injection parameters stored in a memory which may conveniently be recalled instantly and to provide means for retaining the stored parameters in the memory in the event of power interruption to the device.

Another objective of the present invention is to provide a plurality of reliability features, such as parameter verification, self-calibration, and self-testing of the various components of the device in order to improve safety.

A yet further objective of the present invention is to provide means for providing messages from the angiographic injector to the operator, in human readable format.

SUMMARY OF THE INVENTION

To attain the foregoing and additional objectives, the invention comprises a processor-controlled angiographic injector device including a pressure jacket for receiving a syringe containing liquid contrast media, contrast media drive means for forcing the media from the syringe, and processor control system for calculating injection control signals and for controlling the delivery of the contrast media. The processor control system is programmed to elicit injection parameters from an operator or from a pre-programmed storage module and, on the basis of the injection parameters, for calculating the necessary control signals for a closed-loop servo system which actuates the plunger of a syringe. The processor also determines position limits of plunger actuation and effects actuation of a mechanical stop member to block further movement of the plunger when a predetermined volume of media is injected. To improve reliability, actuation of motors for the mechanical stop member and the plunger drive are alternately enabled by a safety relay.

In alternative embodiments of the invention, a pre-programmed storage module is provided for storing routine injection parameters so that they can be instantly recalled. A hardware verification system comprising primary and secondary memories for storing duplicates of injection parameters also is provided. The controller additionally provides multi-phasic injection sequences which involve step-wise changing of the injection parameters (e.g., rate, duration, and/or pressure) during an injection sequence.

Further, the angiographic injector device includes a watchdog circuit which monitors failures in the processor-controlled system, such as in the memories, and the processor itself, and in response to a failure, inhibits the plunger drive means. A self-check feature periodically performs diagnostic routines and a self-calibration feature re-calibrates the servo positioning system when there is a deviation from desired accuracy. To aid in certain types of x-ray photography, such as arteriography or ventriculography, an alternative embodiment of the device includes means for monitoring an ECG waveform and for injecting a small bolus of contrast media at a given rate and pressure during the diastolic interval. Moreover, the alternative embodiment includes an interface circuit for providing external digital communication for transferring either status and/or control information (e.g. injection parameters).

These and other embodiments, aspects, advantages and features of the invention will become apparent upon review of the succeeding disclosure taken in connection with the accompanying drawings. The invention, though, is pointed out particularly by the appended claims.

BRIEF DESCRIPTION OF THE DRAWINGS

FIGS. 7A, 7B, 7C and 7D depict the sequence of the self-test and self-calibrating features under which the automated injector device goes.

DETAILED DESCRIPTION OF ILLUSTRATIVE EMBODIMENT

Figure 1A:
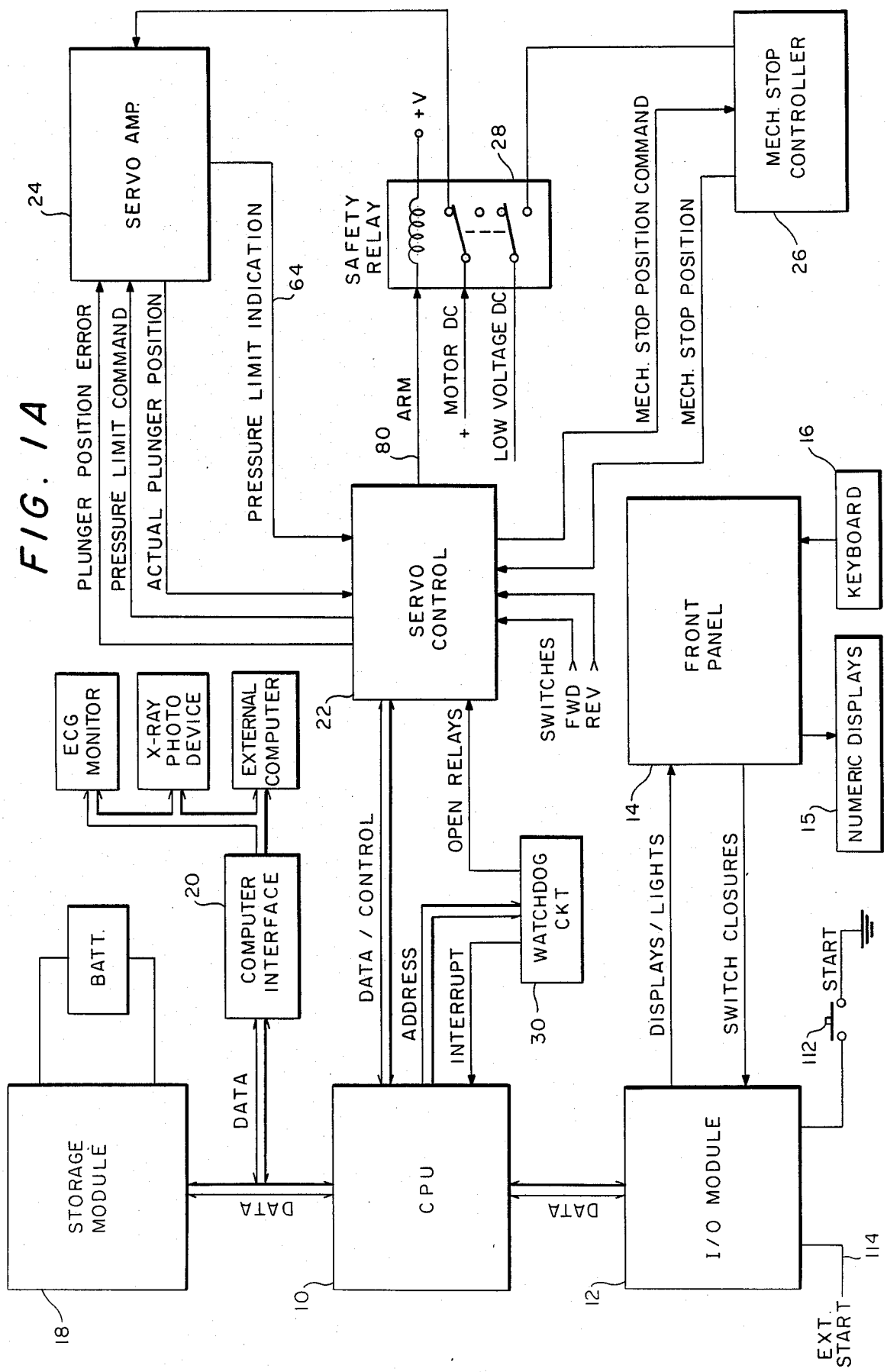
FIG. 1A depicts a block circuit diagram of a preferred embodiment of the invention.

Referring to FIG. 1A, primary functions of the automated angiographic injector device are controlled, monitored and executed by a central processing unit (CPU) 10 such as a commercially known Z80A microprocessor which includes a memory. The memory comprises a read only portion (ROM) such as a 2732 EPROM and a random access portion (RAM) such as a 4016 static NMOS RAM. Coupled to the CPU 10 is an I/O module 12 which, under control of the CPU 10, prompts the operator for certain input parameters and also alerts the operator of error conditions in the system. The I/O module is composed of peripheral devices such as the Zilog Z80-PIO peripheral input/output controller. An indicator panel 14, and keyboard 16 provides operator/injector device interface. In practice, the panel 14 includes a flat sealed membrane to shield electrical switch contacts from contamination. A storage module 18 stores pre-programmed injection parameters which may be instantly recalled and supplied to the CPU 10 when a routine injection procedure is to be performed. The injection module 18 comprises two primary random access memories. Each memory contains a duplicate of the information of the other memory, and prior to an injection procedure, the contents thereof are compared for consistency. If inconsistent, the injection is inhibited.

A computer interface 20 provides external remote communication with the automated injector device and functions to transfer both status information and control information with the device for remote operation and/or monitoring to provide communication compatability with various external devices thereby to facilitate x-ray photography that is synchronized with an ECG waveform. The interface 20 includes, but is not limited to, a standard universal asynchronous receive/transmit port connectible by way of a commercially known RS-232 serial channel or other parallel interface.

The contrast media to be injected into the patient is normally contained in a syringe, the plunger thereof being actuated to force the media therefrom into the vascular system of a patient through a catheter. The delivery rate and volume are normally derived from position signals indicative of the plunger position. Pressure is derived from current supplied to the motor. A servo control network 22 applies a conventional error signal to a servo system for controlling the position of the syringe plunger to control the flow rate and pressure of the contrast media. More specifically, the servo control network 22 supplies error signals to a servo amplifier 24 which energizes a conventional D.C. motor for controlling the position of the plunger.

Also provided for safety enhancement is a mechanical stop controller 26 which, under the control of the CPU 10 and an interlock safety relay 28, automatically positions a mechanical stop member (subsequently described) under control of the CPU 10 to mechanically stop further plunger movement thus preventing additional injection after the desired volume of contrast media has been injected. The safety relay 28 alternately enables the mechanical stop motor and the plunger motor so that one and only one may be operative at a given time. This feature enhances reliability because it ensures that the mechanical stop fully reaches its appropriate position before it is possible to drive the syringe plunger.

Figures 1B, 4:
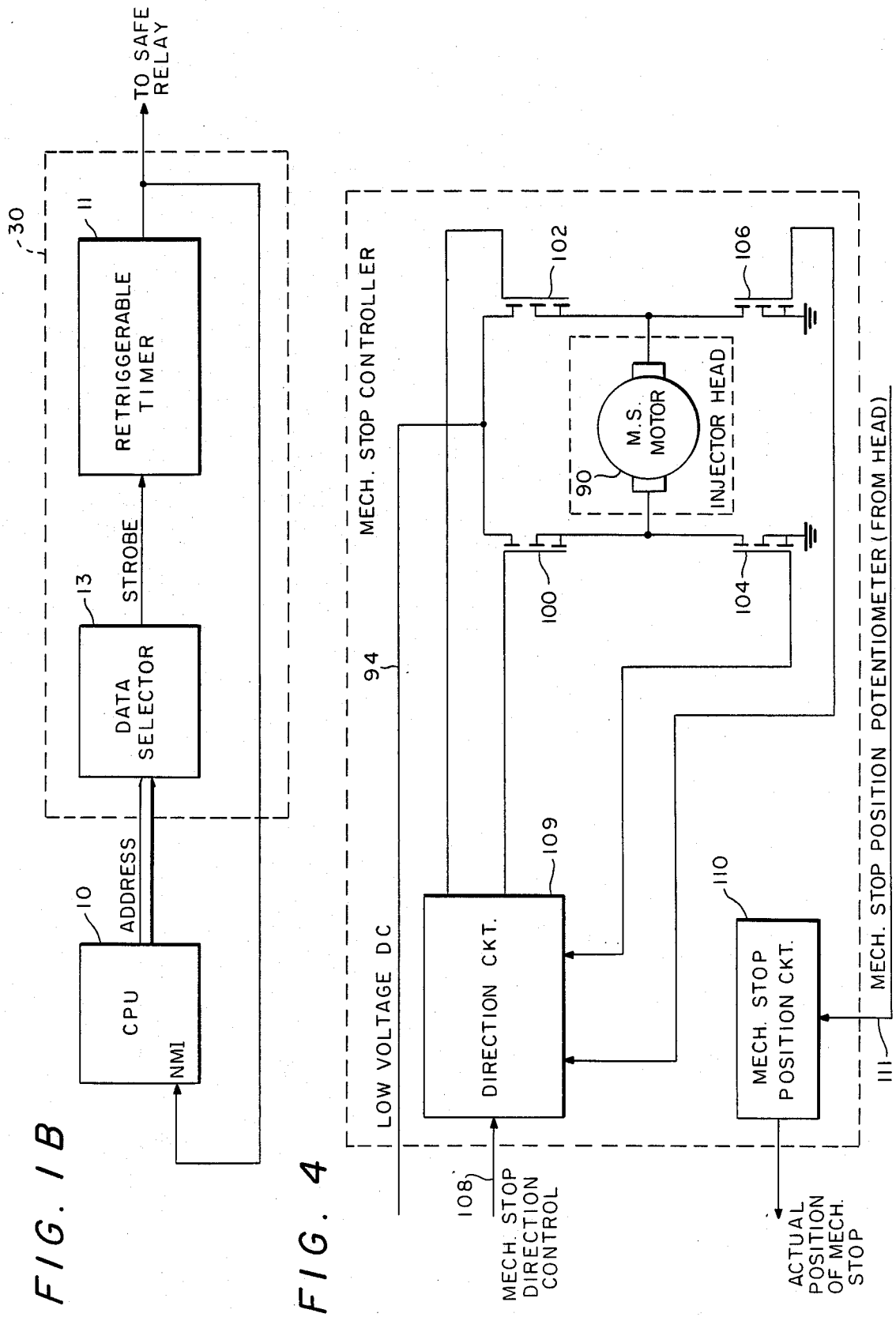
FIG. 1B depicts a watchdog timer circuit of FIG. 1A for monitoring CPU failures.
FIG. 4 depicts a circuit diagram of the mechanical stop controller of the inventive angiographic device of FIG. 1.

A watchdog circuit 30 monitors certain functions of the CPU 10 to effect shut down of the system by inhibiting delivery of contrast media in the event of a failure or a fault. The watchdog circuit, as shown in FIG. 1B, consists of a retriggerable timer (such as a 74123 monostable multivibrator) which generates a pulse after a fixed time interval unless a strobe signal is received from a data selector 13 before the interval elapses. Under normal operating conditions, the CPU 10 executes its control sequence and periodically outputs an address to the data selector 13 (such as 74154) which generates the strobe signal. If a CPU or memory failure occurs, the normal program sequence is interrupted, the data selector 13 is not addressed, the strobe signal is not generated, and the timer 11 is not retriggered. The resulting pulse from the timer automatically opens the safety relay, thereby removing power from the plunger and forcing the processor to execute a non-maskable interrupt (NMI). The NMI forces the CPU 10 to inform the user of a fault condition and then to halt.

Figure 2:
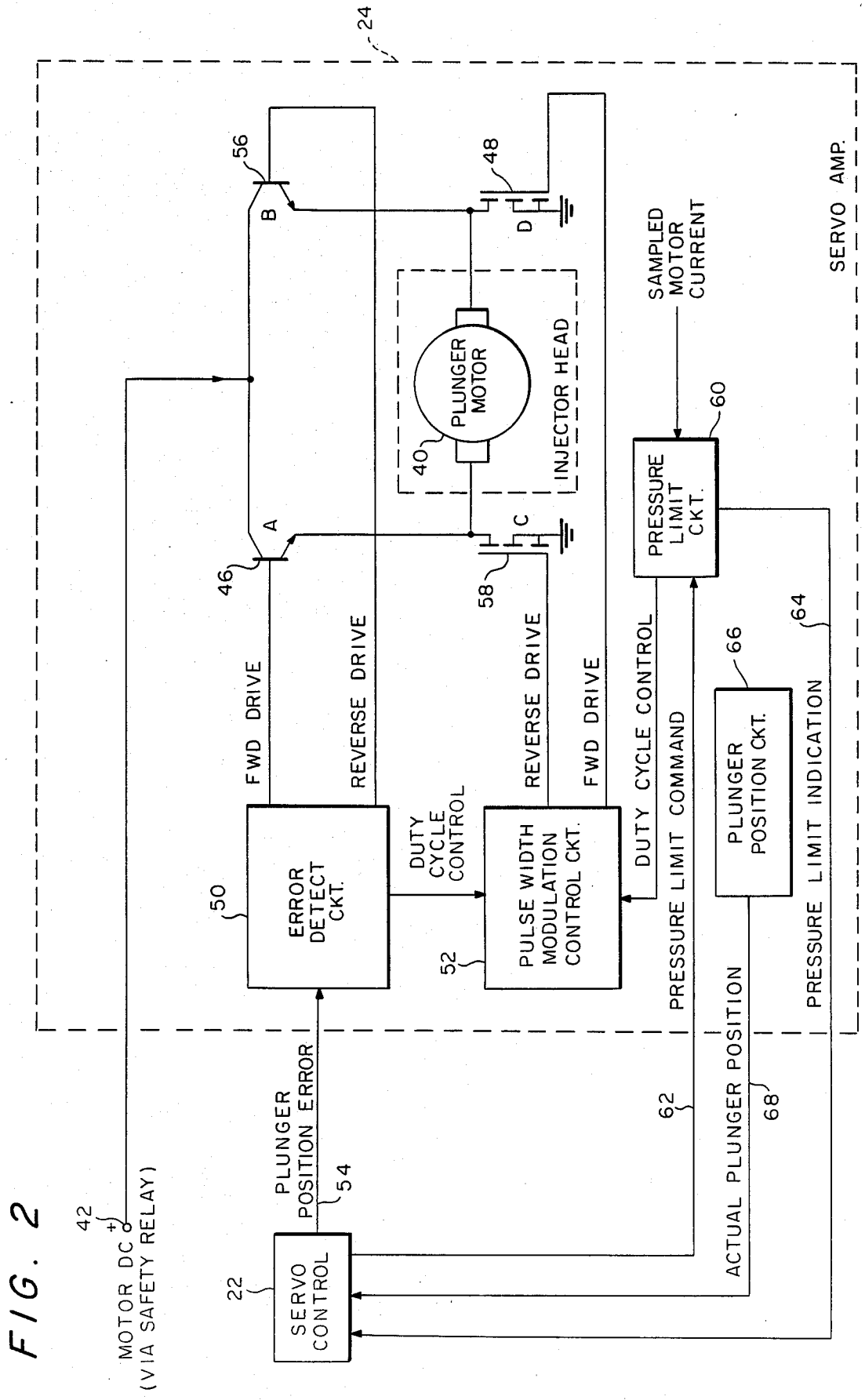
FIG. 2 depicts circuit components of the servo amplifier of FIG. 1.

FIG. 2 depicts the servo amplifier 24 of FIG. 1A. The servo amplifier provides power to move a drive plunger motor 40 under control of digital commands from the CPU 10. The servo amplifier 24 drives a plunger motor 40 which is driven by filtered direct current derived from a series of pulse width modulated current pulses. To drive the plunger motor 40, a D.C. voltage source 42 supplies current to the motor 40 by feeding the respective collectors of transistors 46 and 56. To drive the plunger motor 40 in a forward direction, a position error detect circuit 50 switches on transistor 46 and a pulse-width modulating control circuit 52 delivers a series of enabling pulses to the field effect transistor (FET) 48.

The error signal circuit 76 generates a position error signal from the servo control 22 via a conductor 54. During forward driving of the plunger motor 40, a corresponding set of transistors 56 and 58 is switched off. This allows d.c. current pulses to flow in a forward direction through the plunger motor 40.

To drive the plunger motor 40 in a reverse direction, the error detect circuit 50 switches on transistor 56 and the pulse width modulating circuit 52 pulses the field effect transistor 58. In this fashion, the plunger motor 40 is driven in the reverse direction by the supply of d.c. current pulses in an opposite direction therethrough. Instead of employing FETs 48 and 58, a set of silicon controlled rectilius also can be used.

The position error signal supplied to the servo amplifier 24 over the conductor 54 indicates whether the plunger is ahead of or behind the desired position, and also controls the drive transistors 46, 56, 48 and 58 in an appropriate fashion so that the plunger motor 40 causes the plunger (not shown) of the syringe to track the desired position to maintain the appropriate flow rate, pressure and/or duration. The position error signal is proportional to the magnitude of the difference between the actual position of the plunger and the desired position of the plunger. As the difference increases, so does the width of the drive pulses supplied by the pulse-width modulating circuit 52 to the drive transistors 58 and 48. Thus, when the position error signal is large, the average current supplied to the plunger motor also increases.

The servo amplifier 24 also includes a pressure limit circuit 60 which functions to inhibit the pulse-width modulating circuit 52 and shut down the drive current pulses supplied to the plunger motor 40. The circuit 60 constitutes a control circuit which informs the servo control when the pressure in the syringe exceeds a given set point established by the processor 10. It does so by monitoring motor current which is proportional to the fluid pressure, and operates to reduce the motor velocity of the plunger motor 40 by cutting the duty cycle of pulse-width modulated current pulses when the pressure exceeds a preset limit. The injector device has pressure input means to set and/or display the pressure limit in conventional units of PSI, KPA, KG or ATU. A switch is also provided to select and/or display the selected unit.

Under normal conditions, when the pressure limit has not been exceeded, the servo amplifier 24 causes the plunger position to follow the position command established by the processor 10. A digital-to-analog converter device 74 in the servo control portion of the system sets the pressure limit command. When actual pressure exceeds the programmed pressure limit, the pressure limit circuit 60 asserts a pressure limit indication signal 64 which informs the CPU 10 to stop changing the position command signal. The pressure limit command signal is supplied to the servo amplifier 24 via conductor 62. When the pressure limit signal 64 is no longer present, the CPU 10 retakes control by resuming the transmission of position command signals starting from the known plunger position. The plunger position, derived from a rotary potentiometer or optical encoder, is monitored by a plunger position circuit 66, also embodied in the servo amplifier 24. The output of the plunger position circuit 66 is supplied to the servo control 22 via a conductor 68.

Figure 3:
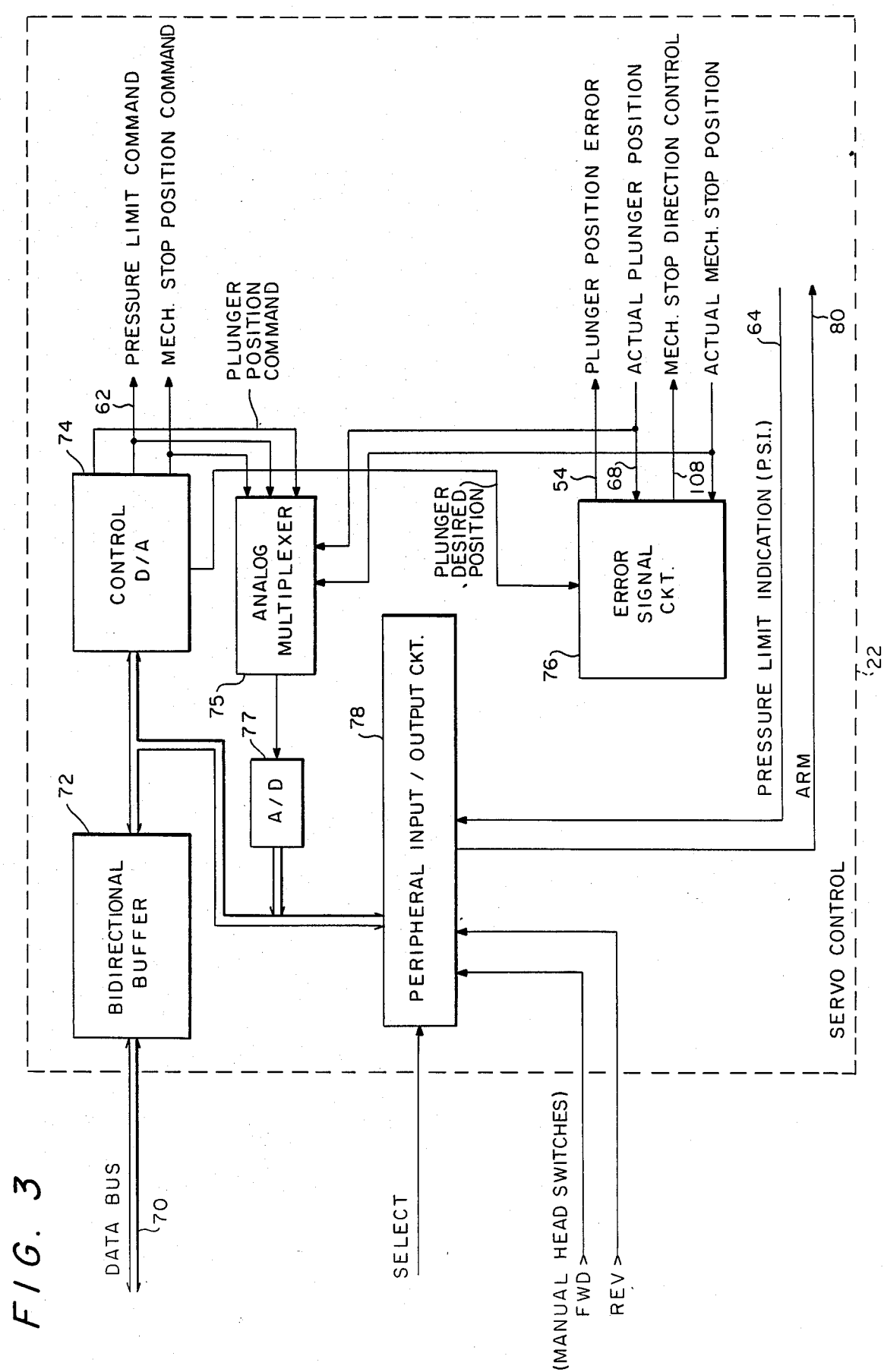
FIG. 3 depicts a functional block diagram of the servo control unit of FIG. 1.

FIG. 3 depicts a servo control circuit 22 in greater detail. The servo control circuit 22 provides an interface between the digital and analog components of the angiographic device. The CPU 10 provides digital position command signals via conductor 70 to a driver bidirectional buffer 72. The digital position command signals are eventually converted to an analog signal by a digital-to-analog converter 74 which are compared by a comparison network in the error circuit 76 which then appears as position error signal on conductor 54. As previously indicated, the plunger position error signal on conductor 54 is supplied to the servo amplifier 24 of FIG. 2.

To perform control and monitoring functions, an analog multiplexer 75, under control of the CPU 10 or a clocking signal, selectively conveys analog output signals from the control D/A circuit 74 or error circuit 76 to an A/D converter 77. The A/D converter 77 converts these signals to digital form and then, in turn, passes them to the CPU 10. The CPU 10 uses these digital signals to perform such functions as calibration, self-testing, and servo control. These functions are subsequently described.

The servo control circuit 22 also regulates the operation of the interlocked mechanical stop/plunger relay in the servo amplifier circuit 24 and the mechanical stop controller circuit 26. A peripheral input/output device 78 in the servo control circuit 22 provides means for transferring status and control signals to alter the operation of the servo amplifier circuit 24 and the mechanical stop controller 26. With respect to the interlocked mechanical stop/plunger relay operation, the input/output circuit 78 removes the plunger ARM signal via conductor 80 when the plunger reaches a predetermined position as determined by the CPU 10 and monitored by the plunger position circuit 66 (FIG. 2). An ARM signal supplied over the conductor 80 is conveyed to the mechanical stop controller circuit 26 to actuate a mechanical stop drive motor which inhibits further plunger movement. This feature also will be subsequently described. The servo control circuit 22 also generates pressure command signals and monitors the pressure limit.

FIG. 4 depicts the mechanical stop controller 26 wherein a mechanical stop motor 90 couples a mechanical stop member to actuate it against the plunger drive mechanism to block movements thereof when a predetermined calculated volume of contrast media has been injected.

Similarly to the plunger drive motor 40 of FIG. 2, in a preferred embodiment, the mechanical stop motor 90 turns a ball screw to drive a mechanical stop plate forward. The drive command is given to drive the mechanical stop motor 90 at full speed until the mechanical stop position indicator on the mechanical stop mechanism indicates that desired position has been attained. This is accomplished by converting a potentiometer position signal supplied over conductor 111 from the stop mechanism to a digital value via an analog/digital converter. When the position signal indicates engagement of the stop plate, the drive command is removed.

Figure 5A:
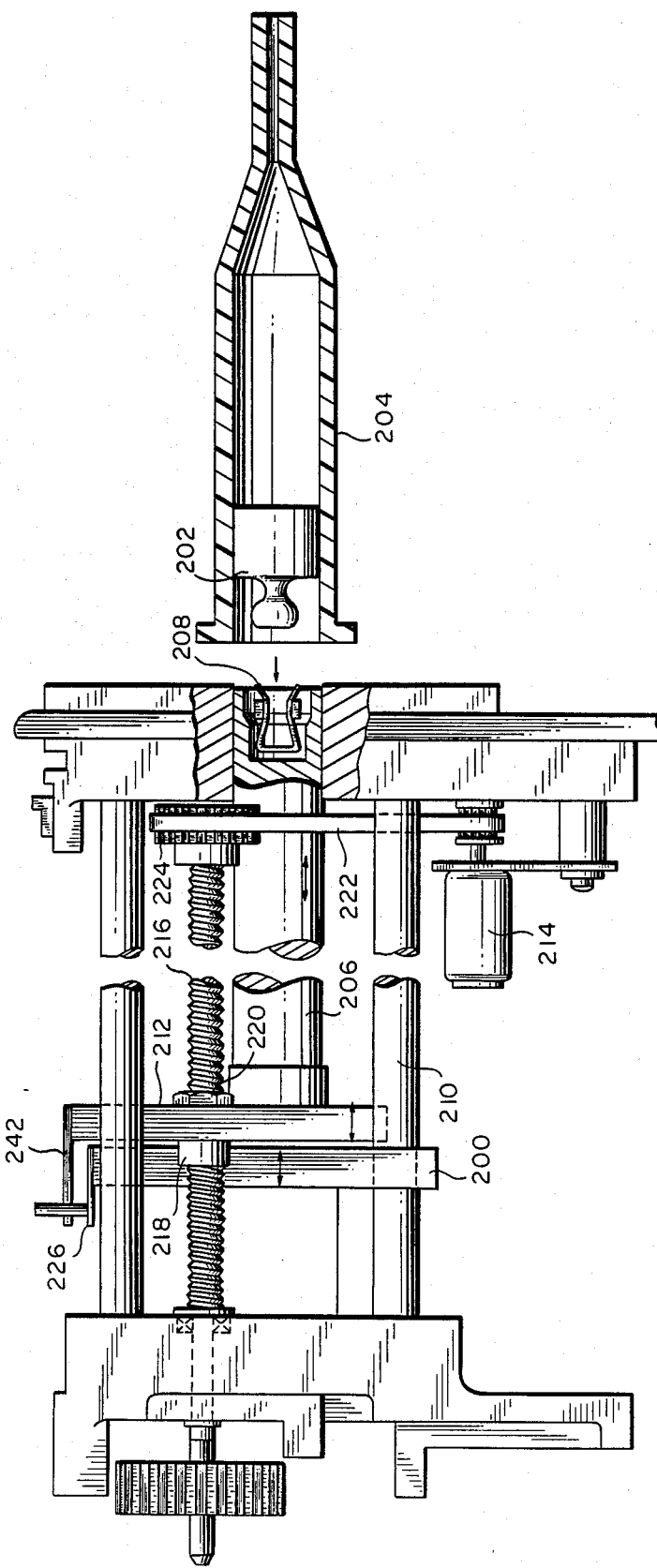
FIG. 5A is a diagram of the mechanical stop mechanism which responds to the controller of FIG. 4 of the angiographic injector device.

FIG. 5A depicts an illustrative mechanical assembly for driving the piston of a syringe containing contrast media. As seen, a movable drive plate 200 actuates a piston 202 of a syringe 204 by way of a shaft 206. Although shown in spaced-apart relation, the piston 202 connects to a spring clip 208 when engaged therewith. The spring clip 208 is fastened to the end of the shaft 206. A plunger drive motor (not shown) corresponding to the motor 40 (FIG. 4) of the controller actuates the shaft 206 through the plunger plate 200. Linear movement of the plunger plate is guided by a guide rod 210.

As previously indicated, a mechanical stop prevents further movement of the drive shaft when a fixed amount of contrast media has been injected. To accomplish this task, a stop member in the form of a plate 212, is prepositioned prior to an injection. Prepositioning is done by a stop motor 214 (corresponding to motor 90 of FIG. 4) under control of the CPU 10. Conventional position transducers in the form of resistive potentiometers supply position information of the stop member 212 to the CPU 10 through an A/D converter.

Actuation of the stop member 212 is done by rotation of shaft 216 having threads mechanically coupled to a bore that is journalled through a bushing 218 held against the stop plate 212 by a nut 220. To rotate the shaft 216, motor 214, when energized, turns a grooved, flexible drive belt 222, which in turn, rotates a drive pulley 224. The pulley 224 connects to the shaft 216.

Figure 5B:
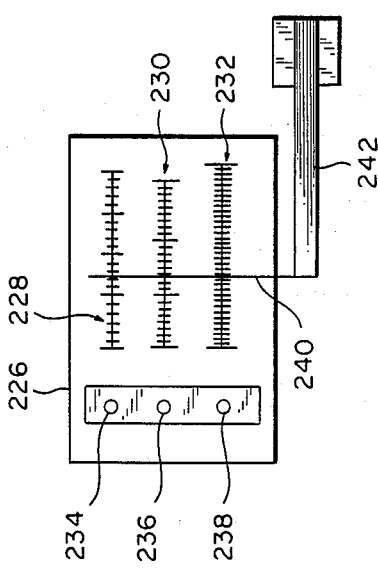
FIG. 5B depicts an arrangement for visually indicating a scaled volume of contrast media ejected from a syringe.

FIG. 5B depicts a system for visually indicating the volume of contrast media injected from a syringe by utilizing different scales. Each scale corresponds to a syringe of a particular size, and the "active" scale is indicated by the appropriate light being energized. A face card 226 contains three separate scales 228, 230, and 232 of different units corresponding to incremental units of media in a syringe 204. Syringes of different diameters yield different units of media for the same linear movement of the plunger 202. To visually indicate which unit applies to a particular syringe, LED indicators 234, 236 and 238 are provided. One of these indicators is activated by a switch to show which scale is active, in which case, a needle 240 carried by arm 242 indicates relative volume injected. The arm 242 connects to the stop plate 212 while the face card 226 connects to the drive plate 200.

As previously indicated, the double-throw, double-pole operation of the relay 28 (FIG. 1A) energizes either the drive motor 90 (FIG. 4) or the plunger drive motor 40, but not both simultaneously. The mechanical stop motor 90 functions similarly to the plunger motor 40 of FIG. 2, in that it includes a set of field effect transistors 100, 102, 104 and 106 which are energized to drive the mechanical stop motor 90 in a forward and/or reverse direction. Direction is controlled by a direction circuit 109 in response to a signal from the servo control 22 supplied via the conductor 108. The mechanical limit of the mechanical stop motor is controlled by a mechanical stop position circuit 110 which responds to a limit switch when the stop plate reaches a forward-most position or rearward-most position.

The CPU 10 controls the system using a microprocessor and associated program for monitoring or eliciting input information (e.g. injection parameters) supplied by an operator and then develops command information to control the injector device. The CPU 10 communicates with the I/O module 12 which interfaces external switches on the front control panel of the system.

The watchdog circuit 30 implements an active system for inhibiting injection of contrast media in the event of a microprocessor failure. The circuit 30 includes a resettable timer which opens the safety relay 44 after a predetermined time period unless the CPU 10 actively resets it, thus allowing this cycle to repeat. Thus, if the CPU 10 fails, the safety relay 44 will be deactivated without further operation of the CPU 10.

The I/O module 12 monitors a manual signal supplied by the operator via a manual start switch 12 or an event signal from an external device supplied over the conductor 114. As previously indicated, the automated angiographic injector device may respond to certain cardiac events by monitoring an ECG signal thereby to actuate, or start an injection, at a predetermined time instance during an ECG cycle. This is done using well known techniques by the external event signal, and is particularly useful during certain cardiac studies.

The control/display panel 14 provides user/device interface for inputting and displaying injection parameters, such as syringe size, flow rate, volume, duration, pressure limit, or rise/fall time. This information can be prompted by the CPU 10 and entered by the operator. The entries are echoed back to the operator for a visual verification on a display of the panel 14. In physical construction, the panel 14 comprises a sealed membrane switch panel that is impervious to fluid spills and wipes clean without damage to switches contained underneath. Prior to an injection, the injection parameters are displayed and verified by an operator. Verification enables, e.g. arms, the injector device, and is preferably accomplished manually by depressing a contact switch associated with each injection parameter. After an injection, the actual values of flow, volume, etc. can be displayed so that the operator may confirm an effective or safe injection.

A pre-programmed injection module 18 provides non-volatile storage of injection parameters. Specific routine angiographic procedures require established flow rates, volumes, pressures and linear rise/fall time, but once these parameters are established, set-up of the angiographic device becomes routine. As an added convenience, these parameters can be stored in the pre-programmed injection module 18 so that an injection can proceed immediately after arming the system without the necessity to re-enter the injection parameters. To enhance reliability of the pre-programmed injection module 18, the stored injection parameters are verified by duplicating the values thereof in an auxiliary memory. Thus, the pre-programmed injection module preferably comprises a primary and a secondary random access memory for storing duplicates of the injection parameters and, prior to an injection procedure, the CPU 10 compares the contents of both memories to verify the parameters. Both memories are maintained with batteries when power is shut down thereby achieving non-volatility.

Figure 6:
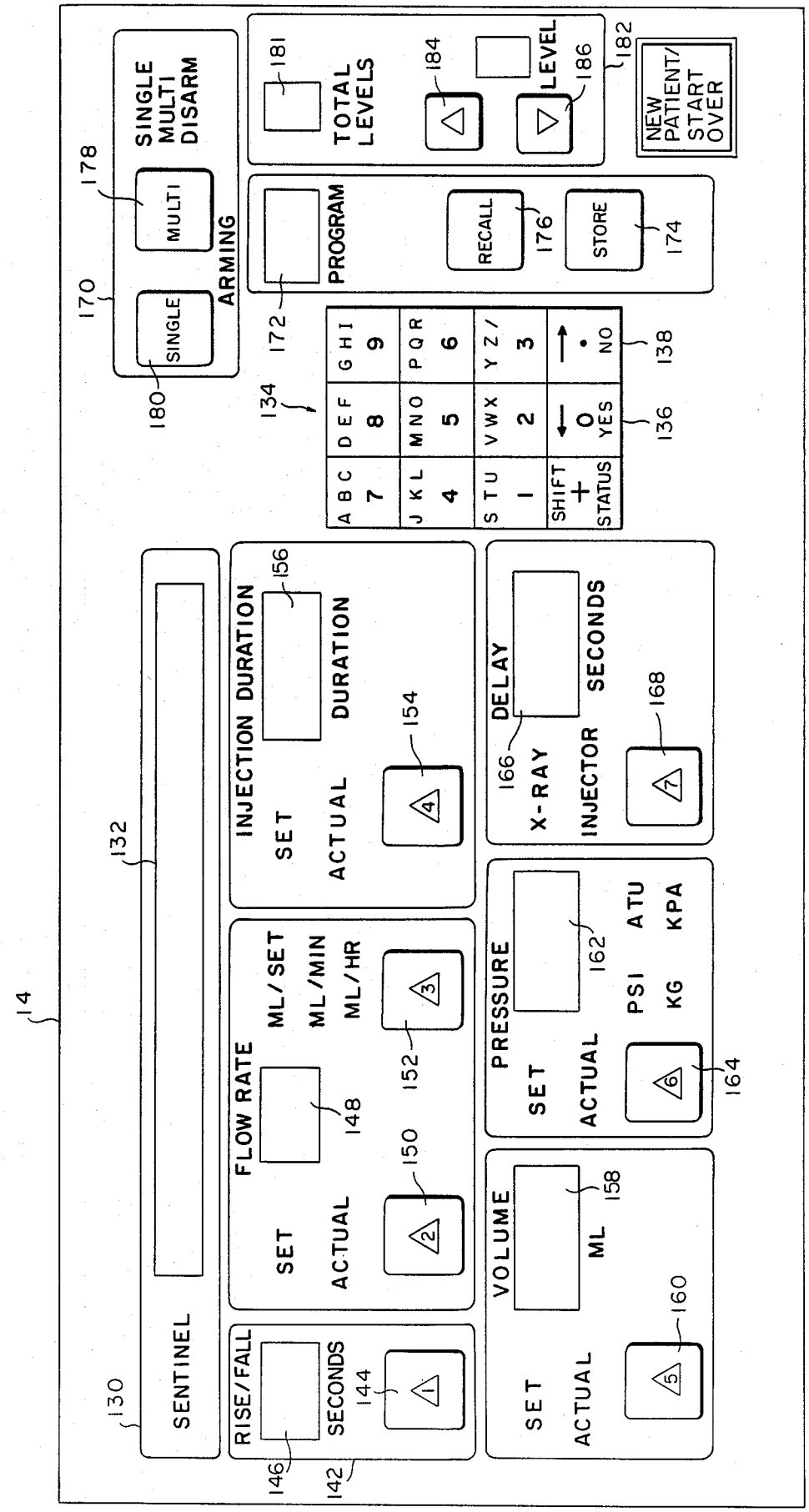
FIG. 6 depicts the front control and display panel of FIG. 1.

FIG. 6 depicts a preferred arrangement of the front panel 14 of FIG. 1 for providing an indication of injection parameters entered, confirmed and/or displayed in the device, and for providing an indication of control-/injection parameters under which an injection had taken place. The front panel 14 preferably comprises a flat, sealed membrane covering switches located beneath the flexible membrane. This structure seals the switches from possible contamination from an external environment.

The front panel 14 includes various sections to facilitate entry of injection parameters and for displaying the status of an injector procedure. Display and entry of information is preferably accomplished in human readable format. Specifically, the front panel 14 includes a sentinel 130 which includes an alphanumeric display section 132. The display section 132 displays, among others, alphabetical and numeric information which is entered into the injector device by way of an alphanumeric keypad section 134. The keypad 134 enables entry of both numeric and character information in a conventional manner. During entry, the information is displayed on the sentinel display section 132.

The front panel also includes a dual function control and display section including an individual input pad 142 for entering and/or confirming, among other parameters, a rise/fall time of flow of contrast media. In operation, once the switch pad 144 is depressed and the desired rise/fall injection parameter is entered into the device, the specific rise/fall injection parameter is displayed in the display section 146. Similarly, a desired flow rate also can be programmed into the injection device. This injection parameter is displayed in a flow rate display 148 and entered into the device by switch input pad 150. The units of flow rate can be entered or displayed in milliliters per second, milliliters per minute, or milliliters per hour under control of a switch pade 152.

The duration of an injection can be entered by depressing the switch pad 154 and then pressing "number" keys on keypad 134. Injection duration is displayed in a display portion 156. Any two of the three parameters, flow, volume, duration, may be entered in any order, and the third then automatically is calculated.

The volume of contrast media to be injected during an injection sequence is displayed in display 158 and is entered and/or confirmed by the switch pad 160. Similarly, the pressure at which the contrast media is to be injected is displayed and/or entered, respectively, by display 162 and switch pad 164. Similarly, x-ray photo delay from the time an injection sequence begins is displayed on display 166 and is entered with switch pad 168 and numerical keypad 134.

To facilitate entry of the injection parameters, the CPU 10 effects flashing of indicator lights located above the switch pads 144, 150, 152, 154, 160, 164, and 168. For example, when the CPU 10 prompts the operator to enter the rise/fall injection parameter, an indicator light above the switch pad 144 flashes. When the appropriate value has been entered and is displayed correctly in the display 146, the switch pad 150 is depressed by the operator, whereupon display 146 ceases to flash and stays lit, while the indicator light over the switch pad 150 begins flashing. The flashing sequence advances to the next injection parameter to be entered as each parameter is entered.

If a processor-recognizable parameter is not entered, the CPU 10 effects generation of an alarm, such as an audible beep and/or error message on display 132. Further, the CPU 10 will prevent further entry or arming of the device until the error has been corrected. As an example, entry of an injection volume that is greater than the syringe size will cause an error. The panel 14 also has a contact switch for clearing the contents of any parameter or information displayed or entered into the injector device.

The front panel 14 further includes an arming section 170 for selecting a single phase or a multi-phase injection sequence. In order to recall routine injection parameters or to store a set of injection parameters, a program section 172 is provided. In operation, once a set of injection parameters is loaded into the device and displayed in the various parameter sections, an identification tag can be generated by way of the keypad 134, displayed in the sentinel 132, and stored in non-volatile memory by depressing the store switch 174. One or more numbers or words, or alphanumeric combinations, can be used to identify a prestored set of injection parameters. The set of injection parameters then is stored in a storage module under the name or number which appears in the sentinel 132 when stored. That same information can be quickly recalled by entering the name or number associated with the previously stored set of injection parameters by depressing recall switch 176.

Then, before the injector can be armed for performing an injection, the operator is required to depress each of the switch pads 144, 150, 152, 154, 160, 164 and 168, to verify the accuracy of the injection parameters being displayed.

During a multi-phasic injection sequence, a number of injections may be performed without disarming the machine after delivery of the programmed injection volume. Each depression of the main start switch 112 will deliver the same volume until insufficient volume remains in the syringe. A switch pad 178 in the arming section activates the device for a multi-phasic injection sequence. A level control section 182 indicates the number of levels in a single phase or multi-phasic injection sequence. The specific level may be incremented or decremented by way of switch pads 184 and 186 and parameters for each level are entered on switch pads 144, 150, 152, 154, 160, 164, and 168. During a single phase injection, the rise/fall time, flow rate, volume, and pressure for each level are delivered until all levels (up to 9) are completed or the injection is terminated. During multi-phasic injections, all levels are delivered in continuous sequence until the injection is complete. Each time the start switch 112 is pressed, the same injection is delivered without first rearming the machine via multi-arm keypad 178.

The central processing unit 10 also provides a self-calibration and a self test feature. Self-calibration allows proper servicing of critical analog/digital and digital-/analog converters in the system. Upon calling up of appropriate software routines, the processor commands a digital/analog converter 74 to transmit a corresponding analog value, which is then switched through an appropriate analog/digital converter 74. The converted value is then compared with the original digital value thereby to allow adjustment of gain and offsets in the servo control system.

The injector allows the user to enter a syringe size which is used to automatically adjust internal machine parameters to deliver the programmed flows, volumes, and pressures. Syringe size entry is made by answering questions posed by the sentinel display 132 although automatic detection of size may be accomplished by means of mechanical switches located behind the turret assembly.

Likewise, a self-test feature of the invention embodies software routines executed by the central processor 10 which initiates checks of the electrical components, such as the memory, address and data busses, device decoding and checks the accuracy of the data conversion hardware. These functions are accomplished by conventional hardware and specialized software routines, the latter being described in the flow charts of FIGS. 7A, 7B, 7C and 7D. If failures are detected by CPU 10, an appropriate diagnostic message appears on sentinel display 132 to aid in repairing the machine.

FIGS. 7A, 7B, 7C and 7D depict the sequence of the self-test and self-calibrating features under which the automated injector device operates.

Figures 7A, 7B:
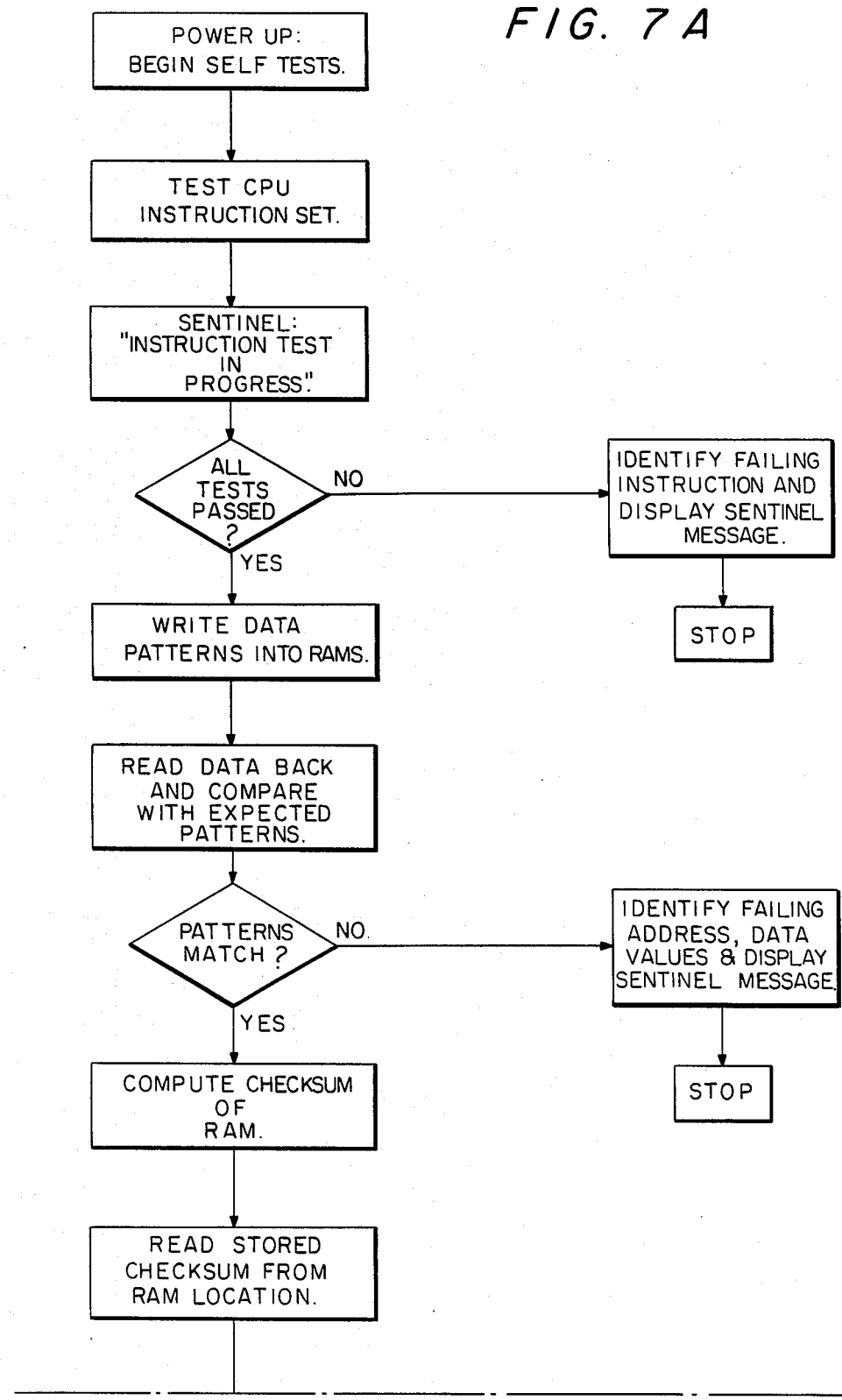

As shown in FIG. 7A, during power-up the system begins a self-test of the circuits. The CPU 10 begins a test of the instruction set and the sentinel 130 displays the message "INSTRUCTION TEST IN PROGRESS". At this point, the system decides whether all test have passed. If not, the instructions failing the test are identified and a message is displayed on the sentinel 130. Now, the system stops or shuts down.

If the instruction sets pass the appropriate test, then the data patterns are written into the RAM memories. After all the data patterns have been written into the RAM memories, another test is begun. During this test, the data is read back and compared with expected patterns. If the patterns do not match, then the failing addresses and data values are identified and a message is displayed on the sentinel 130. The system then shuts down.

As shown in FIG. 7B, after the patterns are found to match, a checksum of the RAM is computed. The checksum is read from the ROM location and if the checksums do not match, then the sentinel 130 will display the message "ROM ERROR" and the system will shut itself down. If the checksums do match, then the pre-programmed memory and the back-up memory are read and compared. If an agreement is not reached then the watchdog circuit generates a non-maskable interrupt and a message is displayed on the sentinel 130. Again, the system will shut down, at this point. If there is an agreement, then a checksum of the pre-programmed memory is computed and compared with the checksum for the pre-programmed memory.

If the comparison is negative, then the sentinel will display a message "PRE-PROGRAMMED MEMORY ERROR" and the system then shuts down.

At this point, if all the tests and checksums are passed, the data stored in the memories will be correct and the memories should be free from errors. As shown in FIG. 7C, the patterns are then loaded into the digital to analog converters. The patterns are converted to analog values. Next, the analog values are transferred through a mixer. From the mixer, the analog values are loaded into an analog to digital converter. The values are converted to digital values. Next, the digital values are read from the analog to digital converter and compared with the original digital patterns. If the digital values do not match, then the data path is identified and the sentinel 130 displays a message. The system then shuts down.

If the digital values do match, then the voltages from the mechanical stop and the plugger pots are checked. This check is to determine whether there is an open or short. If there is, then a message is displayed on the sentinel 130 and the system shuts down.

If there is not, then then sentinel 130 displays the message "READY". At this point the system waits and checks for an injection. If one is not in progress, then the system continues in a loop until an injection is started.

Figure 7D:
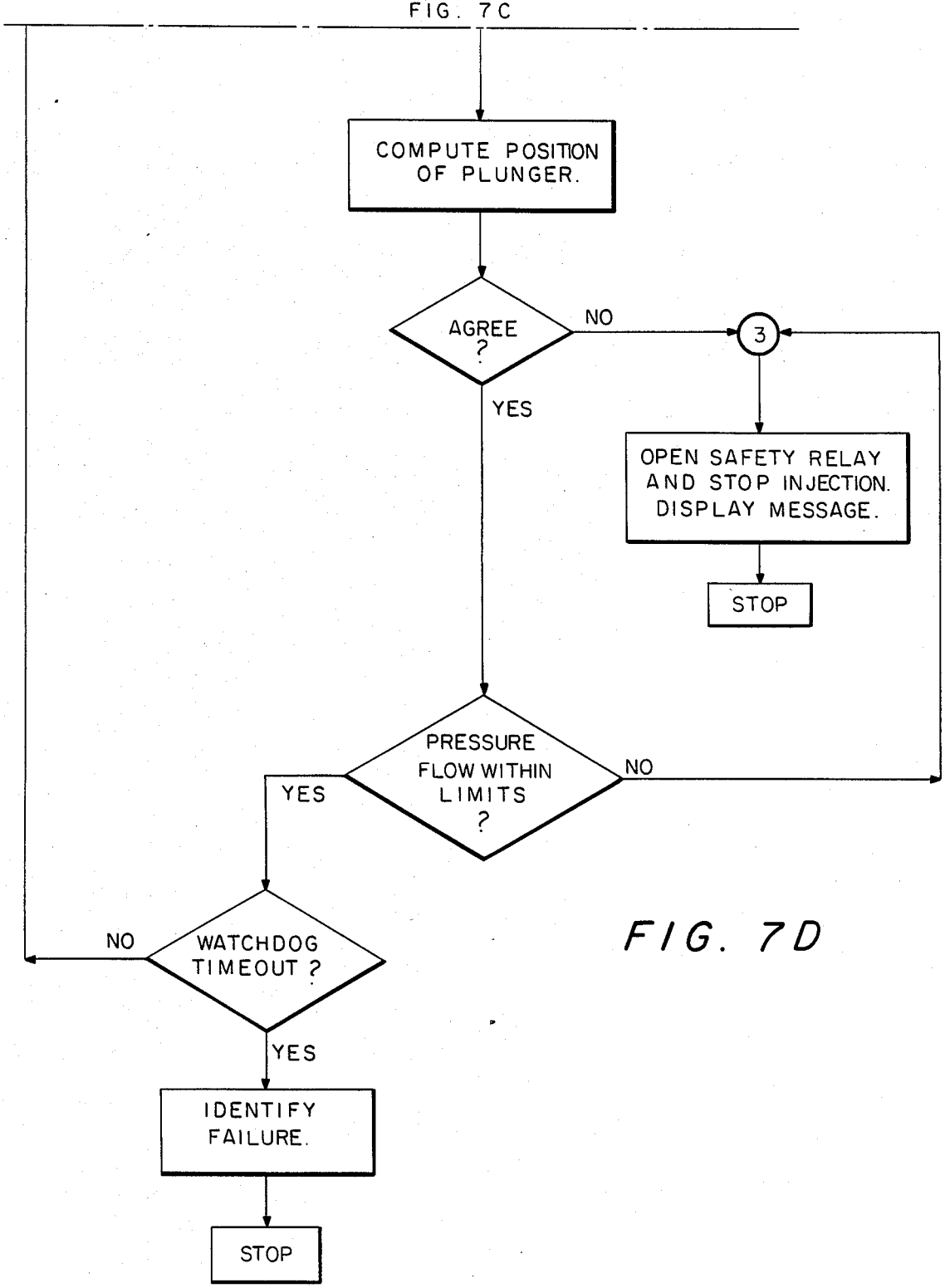

When the device is to be used, a sample of the actual plugger position is taken and used to compute the actual position of plugger. As shown in FIG. 7D, these two positions are compared and if no agreement is reached then the safety relay 28 is opened, a stop injection message is displayed, and the system then stops.

If the actual position and the sample plugger position match, then the pressure flow is tested to determine whether it is within limits set by the operator. If no, then the system opens the safety relay 28 and stops the injection while displaying an appropriate message.

If the system is within the pressure flow limit set by the operator, then the watchdog circuit 30 starts. If the watchdog circuit 30 times out, a failure is identified and the system stops. If the watchdog timer 30 does not time-out, the system returns, as shown in FIG. 7c to position marked 2 and begins the loop of waiting for the previously discussed injection. Now, the system has completed the sequences of self-test and self-calibrating routines. The system is set up for the operation of the processor control injection procedure.

FIGS. 8A, 8B, 8C and 8D are flow diagrams showing the general operational sequence of the automated injector device for performing an injection as described above.

FIGS. 8A, 8B, 8C and 8D show flow diagrams of the operation of the processor control injection procedures. At this point, the system is powered up, all the displays have been cleared to zero, all the back lights are off, the total levels equal one, the level is equal to one and the sentinel 130 displays the message "READY" to prompt the operator.

The system first checks to see if the rise/fall button has been pressed by the operator. If yes, the rise/fall light, on the sentinel 130, flashes and the system waits for the operator to enter the number of seconds which can be set in the range of 0.0 to 9.9 seconds.

Next, the system checks to see if the flow rate button has been pressed. If yes, the rise/fall light stays on, the "set" light flashes and the operator enters a time period of anywhere from 0.0 to 9.9 seconds.

Next, the system checks to see if the flow unit button has been pressed and waits for the operator to select milliseconds, milliminutes or millihours.

Next, the system checks to see if the duration button has been pressed. If yes, the flow rate light stays on the duration "set" light flashes and the system waits for the operator to enter a time period of anywhere from 0.0 to 999.9 seconds. The system begins to calculate the volume and displays this calculation on the sentinel 130 under "VOLUME".

Figure 8A:
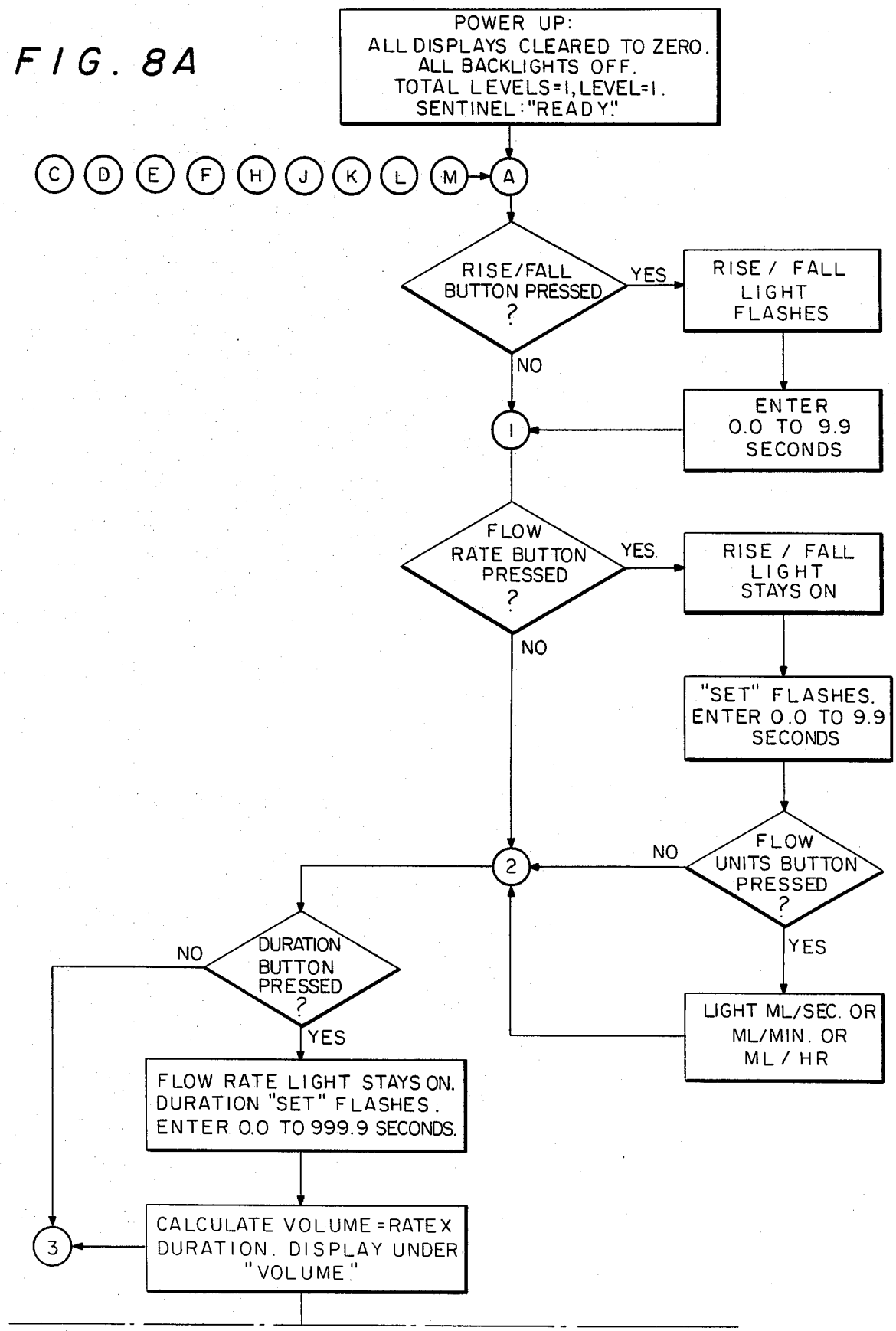
FIGS. 8A, 8B, 8C and 8D show flow diagrams of the operation of the processor controlled injection procedures.
Figure 8B:
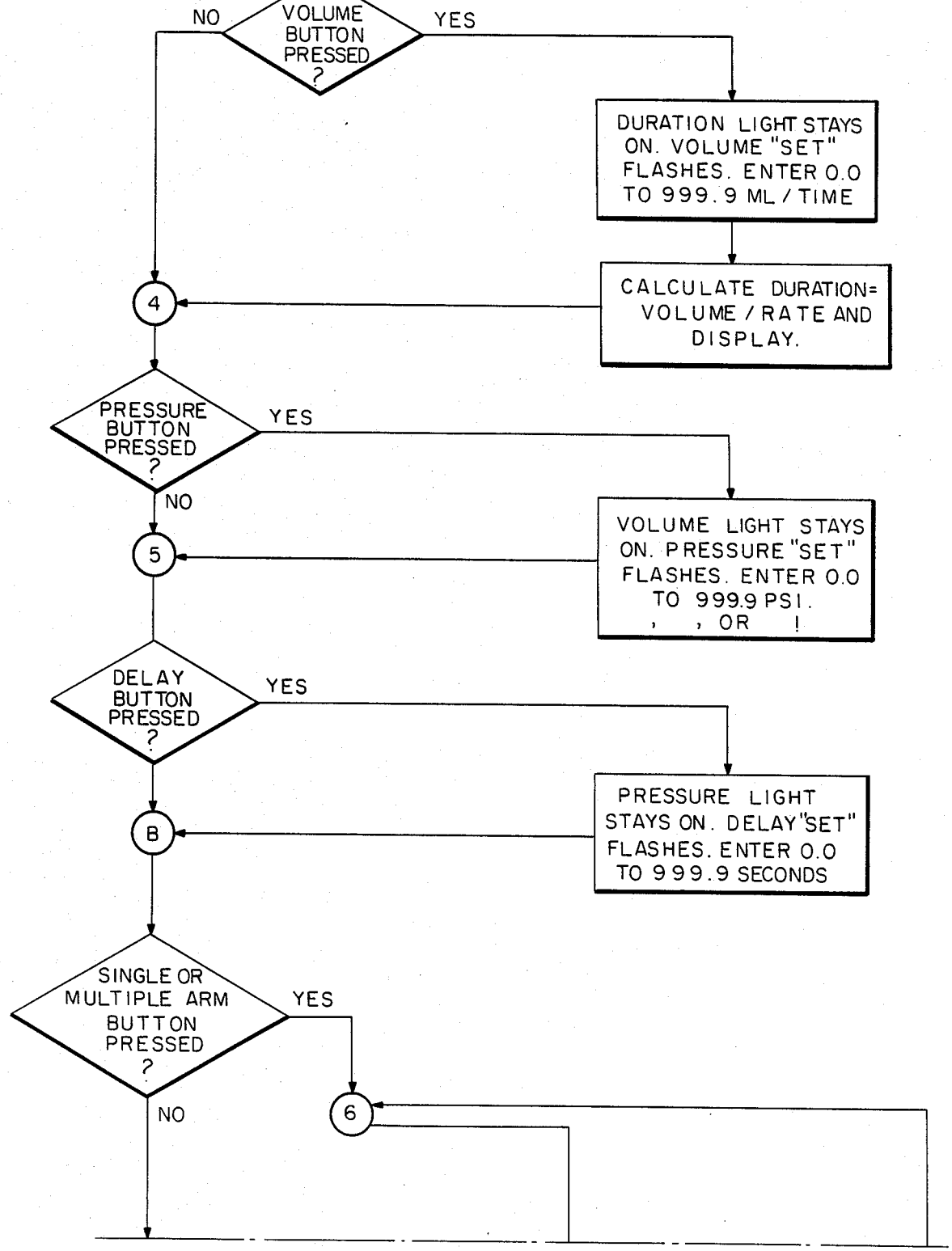

As shown in FIG. 8B, the system checks to see if the volume button has been pressed. If yes, the duration light stays on, the volume "set" light flashes and the operator enters 0.0 to 999.9 ml/time. The calculation of DURATION=VOLUME/RATE is begun and the result of the calculation is displayed.

Next, the pressure button is checked. If it has been pressed, then the volume light stays on, the pressure "set" light flashes and the operator enters the appropriate pressure in the range of 0.0 to 9999 psi.

Next, the delay button is checked to see if it has been pressed. If yes, the pressure light stays on, the delay "set" light flashes and the system waits for the operator to enter the appropriate delay in the range of 0.0 to 9999.9 seconds.

Figure 8C:
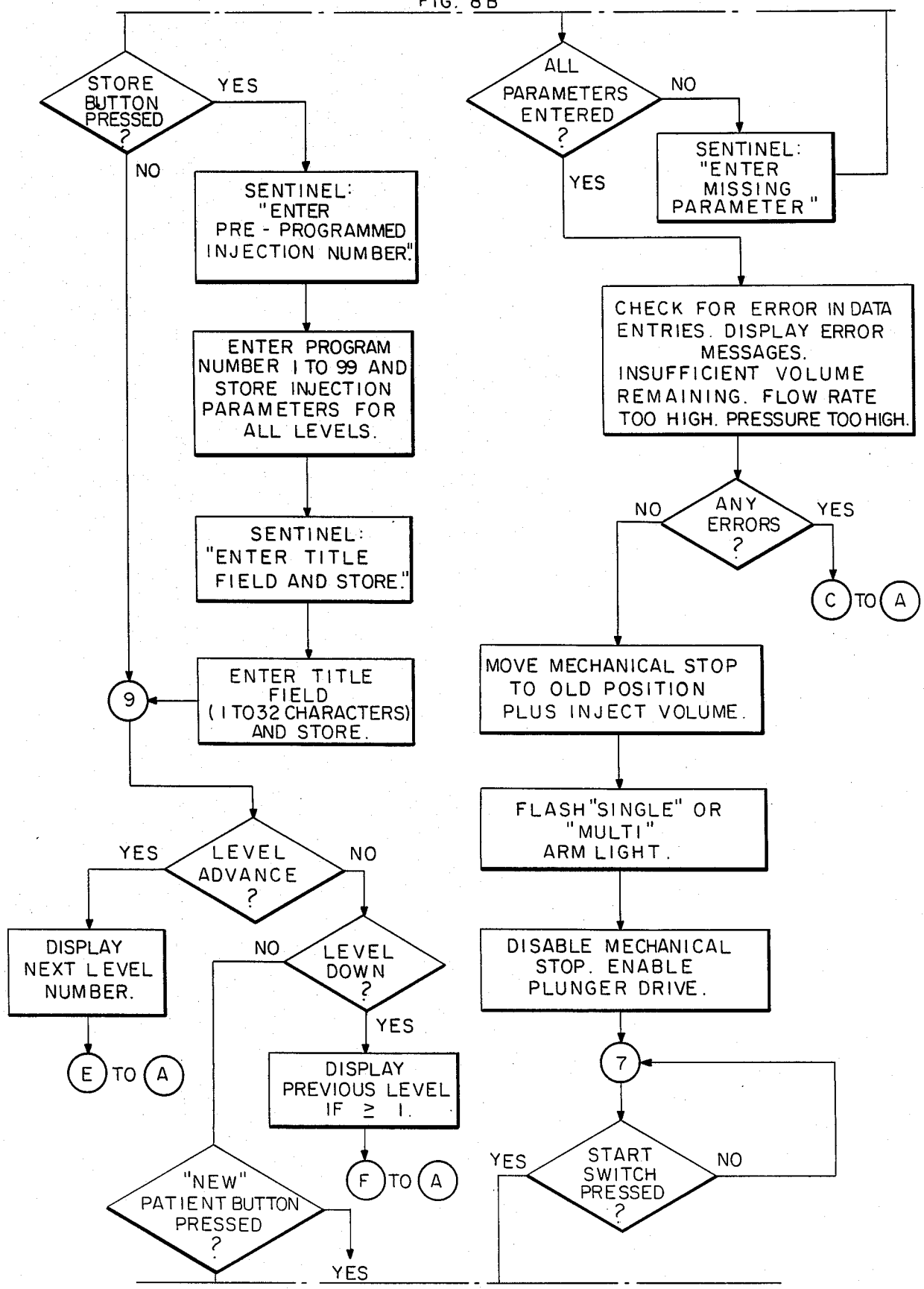

Next, the system checks to see whether the single 180 or multiple 178 button 170 has been pressed. If yes, then as shown iN FIG. 8C, the system will begin to check if all the parameters have been entered. If not, then the sentinel 130 will flash to the operator a message such as "ENTER MISSING PARAMETERS". The system begins a loop and continually checks to see whether all the parameters have been entered.

After all the parameters have been entered, the system checks for errors in the data entries. The system will display error messages such as "INSUFFICIENT VOLUME REMAINING", "FLOW RATE TO HIGH" or "PRESSURE TO HIGH". If there are any errors, then the system returns to the beginning of the routine as illustrated in FIG. 8A and begins by checking if the rise/fall button has been pressed.

If the single or multiple arming button 170 has not been pressed, the system checks to determine whether the store button 174 has been pressed. If it has, then the sentinel 130 displays the message "ENTER PRE-PROGRAMMED INJECTION NUMBER". The operator then enters and the system waits for a program number 1 to 99 and stores injection parameters for all levels at this program number. The sentinel 130 then displays the message, "ENTER TITLE FIELD AND STORE" and the operator enters a title field, comprising 1 to 32 characters, and the system stores these title fields.

Next the system checks to see if there is any level advances, if yes, then it displays the next level number. At this point, the system returns to the beginning of the routine as illustrated in FIG. 8A and once again checks if the rise/fall button has been pressed.

If there are no level advances, then the system checks whether the level is down, if yes, the system displays the previous level. If the level is greater than or equal to 1, then the system returns to the beginning of the routine and checks whether the rise/fall button has been pressed, as illustrated in FIG. 8A.

Figure 8D:
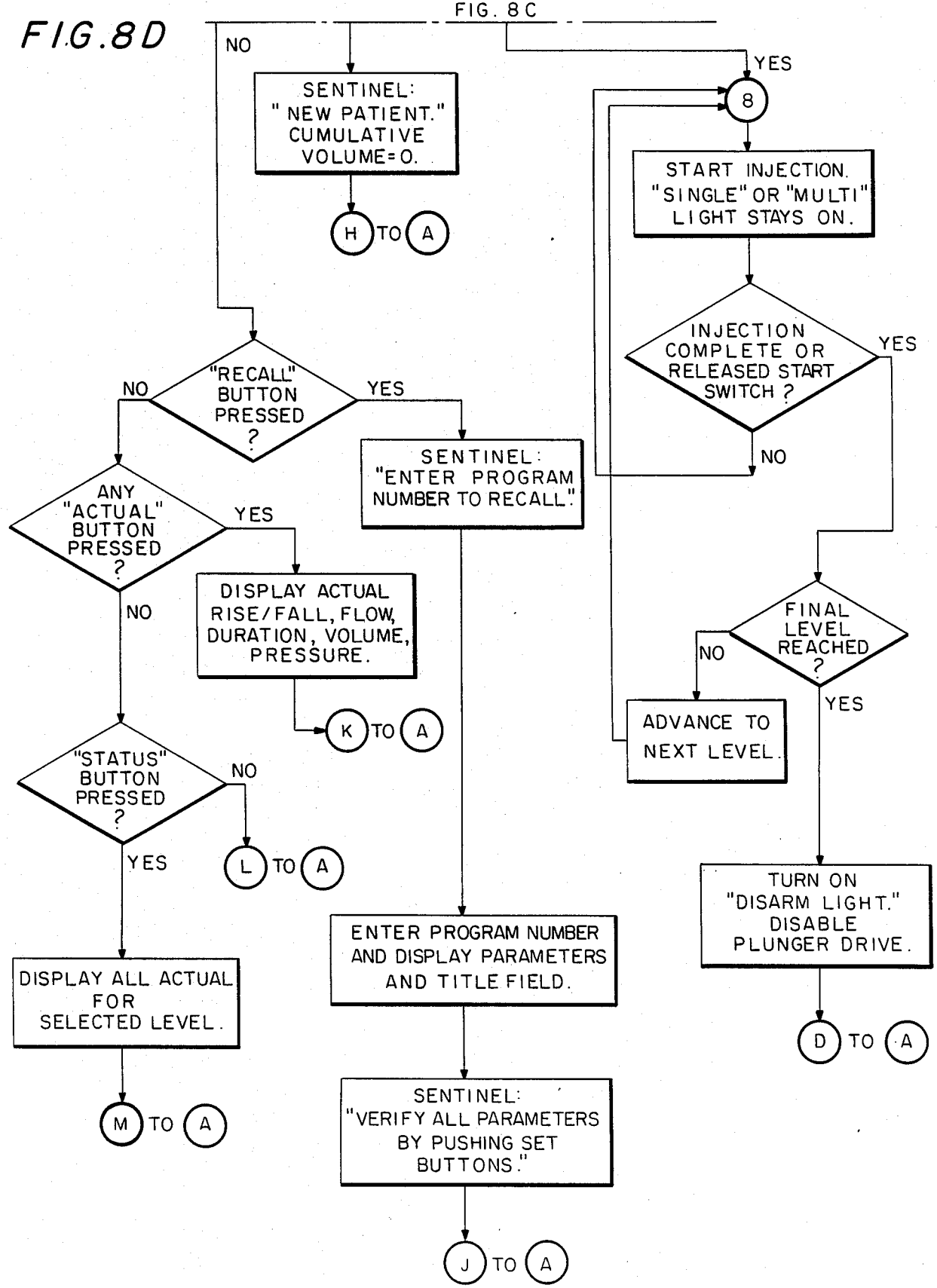

If the level is not down, then the system checks to see whether the new patient button has been pressed. As shown in FIG. 8D, if the answer is yes, the sentinel 130 will display the message "NEW PATIENT" and the cumulative volume is set to zero. The system then returns to the beginning of the program and checks the rise/fall button. If the new patient button has not been pressed, the system checks to see whether the recall button 176 has been pressed. If yes, the sentinel 130 displays the message "ENTER PROGRAM NUMBER TO RECALL". The operator then enters the program number and the system displays the parameters and title field. The sentinel 130 then displays the message "VERIFY ALL PARAMETERS BY PUSHING SET BUTTONS". The system then returns to the beginning of the routine, as illustrated in FIG. 8A, and the system test to determine if the rise/fall button has been pressed.

If the recall button 176 has not been pressed, then the system test to see if an actual button has been pressed. If yes, the system displays the actual rise/fall, the flow, the duration, the volume, and the pressure. The system then returns to FIG. 8A and checks to see if the rise/fall button has been pressed.

If the actual button has not been pressed, then the system checks to see if the status button, on the alphanumeric keypad 134, has been pressed. If no, the system returns to the beginning of the program and checks to see if the rise/fall button has been pressed. If the status button has been pressed, then the system displays all actual values for the selected values. The system then returns to the beginning of the program and checks to see if the rise/fall button has been pressed.

Returning to FIG. 8C, the system checks to see if any errors have been found. If no, the mechanical stop is moved to the old position and selected volume is injected. The system then flashes "SINGLE 180" or "MULTI 178" arming lights. The system then disables the mechanical stop which enables the plunger drive.

At this point the system determines whether the start switch has been pressed. If no, the system begins a closed loop continually checking whether the start switch has been pressed. If yes, as shown in FIG. 8D, the system begins the initial injection process. The "SINGLE 180" or "MULTI 178" light remains on. The system checks to see whether the injection is complete or whether the start switch has been released. If not, the system will continue to loop until the injection has been completed or the start switch has been released. When this step is completed, the system then checks whether the level has been reached. If no, the system then advances to the next level and returns to begin the loop of start injection.

If the final level has been reached, the system then turns on the "disarm" light and disables the plunger drive. The system then returns to the beginning of the routine, as indicated in FIG. 8A, and checks whether the rise/fall button has been pressed.

In view of the foregoing disclosure, it is seen that the specified advantages are obtained by providing automated control of an angiographic injector device. The disclosure hereof is illustrative and is not intended to limit the scope of the invention. Several modifications, changes and adaptations can be made by those skilled in the art without departing from the scope of the invention. For example, the data acquisition modules essentially comprises analog-to-digital and digital-to-analog converters, but are not limited to the same. These may be substituted by other types of data acquisition units to obtain information to provide the control of duration, flow rate and pressure of contast media. Likewise, a closed-loop servo control system is shown, but the invention may be practiced with other types of control systems. Accordingly, it is the intent of each inventor to include all such modifications as may come within the true scope of the invention which is defined by the appended claims.

I claim:

1. An angiographic device for injecting contrast media into the vascular system of a patient, said device comprising: a syringe having a reservoir containing the contrast media, a discharge port through which the media is discharged, piston means for forcing the media through the discharge port from the reservoir, drive means including a d.c. servo motor operatively connected to the piston means for effecting said discharge of the media, receiving means for receiving at least one injection control parameter, and processor control means for generating at least one injection control signal as a function of said at least one injection parameter supplied thereto and for supplying said at least one control signal to said drive means to effect controlled discharge of the media, a servo system governed by a processor position command signal produced by said processor control means, pressure limit means responsive to a pre-established pressure limit signal for inhibiting control of said servo system by the position command signal when pressure in said reservoir exceeds a value represented by said pre-established limit signal, said pressure limit means including means to receive said pre-established pressure limit signal in units of PSI, KPA, KG or ATU, switch means cooperatively interconnected with the means to receive for selecting one of said units of said pre-established pressure limit signal, said processor control means including means for supplying to said d.c. servo motor a d.c. current derived from a pulse-width-modulated drive current and means for establishing a duty cycle proportional to the difference between the actual and the desired positions of said piston means during injection of the media, and mechanical stop controller means interconnected with the processor control means and responsive to a pre-established forward limit of said piston means determined by the processor control means for inhibiting said drive means from discharging the media from the reservoir of the syringe, said mechanical stop controller means comprising a stop member and a d.c. control motor operatively connected to said stop member, means for monitoring the position of said piston means, means for producing a stop command signal when the position of said piston means reaches said forward limit, and means responsive to said stop command signal to actuate said control motor and thereby selectively advance said stop member to mechanically prevent forward movement of the piston means.

2. An angiographic injector device as recited in claim 1, wherein said pre-established forward limit of said stop member is established in dependence on the value of said at least one injection control parameter supplied thereto.

3. An angiographic injector device as recited in claim 2, further including safety relay means for alternatively enabling said drive means and said mechanical stop controller means thereby to prevent movement of said drive means while said mechanical stop controller means is actuated.

4. An angiographic injector device as recited in claim 3, further comprising an indicator means for indicating the positions of said mechanical stop member and said piston means relative to each other.

5. An angiographic injector device for infusing a contrast medium into the vascular system of a patient, comprising a syringe enclosing a reservoir holding the contrast medium therein and having a port from which the contrast medium is discharged, said syringe including piston means for discharging the contrast medium from the port in response to displacement thereof, drive means operatively connected to the piston means for effecting said displacement thereof, means for monitoring said displacement of the piston means to a limit position, signal generating means operatively connected to the monitoring means for producing a stop command signal in response to the piston means reaching said limit position during said displacement thereof, a stop member engagable by the piston means in the limit position thereof, controller means operatively connected to the stop member for selectively positioning said stop member to establish said limit position, and means operatively connected to the controller means and responsive to said stop command signal for disabling the drive means to prevent continued displacement of the piston means beyond the established limit position.

6. In a system for infusing contrast media from a syringe reservoir through a catheter into a vascular system of a patient by means of a plunger acting against load conditions dependent on plunger resistance, syringe reservoir volume, contrast media viscosity and catheter length and flow area, powered drive means operatively connected to the plunger for displacement thereof to effect infusion at a predetermined flow rate and pressure, servo means connected to said drive means for establishing said predetermined flow rate and pressure in accordance with a plurality of injection control parameters independent of said load conditions, means for selecting said injection control parameters pursuant to which the predetermined flow rate and pressure is established to controllably change the flow rates and pressures under which the contrast media is infused, and including mechanical stop means engagable by the plunger for limiting displacement thereof to a limit position and controller means operatively connected to the mechanical stop means and the servo means for establishing the limit position in accordance with a selected one of the injection control parameters.

7. The system as recited in claim 6, wherein said selecting means includes multi-level control means for sequentially changing the injection parameters during infusion.

8. An angiographic injector device as recited in claim 7, further including means for pre-establishing a rise/fall time of pressure level of said contrast media between successive phases of a multi-phasic injection sequence.

9. An angiographic injection device as recited in claim 6, including means for monitoring an ECG waveform representative of a cardiac cycle of the patient, and means for automatically effecting injection of a given quantity of the media at a controlled rate during a given time interval of said cardiac cycle to facilitate x-ray photography synchronized with said ECG waveform.

10. In a system for infusing contrast media from a syringe reservoir through a catheter into a vascular system of a patient by means of a plunger acting against load conditions dependent on plunger resistance, syringe reservoir volume, contrast media viscosity and catheter length and flow area, powered drive means operatively connected to the plunger for displacement thereof to effect infusion at a predetermined flow rate and pressure, servo means connected to said drive means for establishing said predetermined flow rate and pressure in accordance with a plurality of injection control parameters independent of said load conditions, mechanical stop means engagable by the plunger for limiting displacement thereof to a limit position and controller means operatively connected to the mechanical stop means and the servo means for selectively establishing the limit position prior to said displacement of the plunger.

11. The system as defined in claim 10 wherein said operational condition is loading pressure of the media during said infusion thereof.

12. The system as defined in claim 11 wherein said servo control means includes means for limiting flow of the media in accordance with said injection parameter.

13. An angiographic injector device for infusing a contrast medium into the vascular system of a patient, comprising a syringe enclosing a reservoir holding the contrast medium therein and having a port from which the contrast medium is discharged, said syringe including piston means for discharging the contrast medium from the port in response to displacement thereof, drive means operatively connected to the piston means for effecting said displacement thereof, means for monitoring said displacement of the piston means to a limit position, signal generating means operatively connected to the monitoring means for producing a stop command signal in response to the piston means reaching said limit position during said displacement thereof, a stop member engagable by the piston means in the limit position thereof, controller means operatively connected to the stop member for positioning thereof to establish said limit position, means operatively connected to the controller means and responsive to said stop command signal for disabling the drive means to prevent continued displacement of the piston means beyond the established limit position, and interlock means for alternately enabling the drive means and the controller means to prevent operation of the drive means until said limit position is established by the controller means.

14. In a system for infusing contrast media from a syringe reservoir through a catheter into a vascular system of a patient by means of a plunger acting against load conditions dependent on a plunger resistance, syringe reservoir volume, contrast media viscosity and catheter length and flow area, powered drive means operatively connected to the plunger for displacement thereof to effect infusion at a predetermined flow rate and pressure, servo means connected to said drive means for establishing said predetermined flow rate and pressure in accordance with a plurality of injection control parameters independent of said load conditions, mechanical stop means engagable by the plunger for limiting displacement thereof to a limit position, controller means operatively connected to the mechanical stop means and the servo means for establishing the limit position prior to said displacement of the plunger, and interlock means for atlternatively enabling the drive means and the controller means to prevent said displacement of the plunger until said limit position is established through the controller means.

15. In a system for infusing contrast media from a syringe reservoir through a catheter into a vascular system of a patient by means of a plunger acting against load conditions dependent on plunger resistance, syringe reservoir volume, contrast media viscosity and catheter length and flow are, powered drive means operatively connected to the plunger for displacement thereof to effect infusion at a predetermined flow rate and pressure, servo means connected to said drive means for establishing said predetermined flow rate and pressure in accordance with a plurality of injection control parameters independent of said load conditions, means for selecting said injection control parameters pursuant to which the predetermined flow rate and pressure is established to controllably change the flow rates and pressures under which the contrast media is infused, said injection control parameters selected from a group including flow rate of the contrast media, volume of the contrast media, duration of infusion, pressure limit of said contrast media, x-ray photo delay, inject delay and flow rise/fall time of pressure of the contrast media, primary memory means for storing said at least one injection parameter, secondary memory means for storing a duplicate of the contents of said at least one injection parameter, and parameter verification means for comparing the injection parameters of said primary and secondary means and for inhibiting said drive means when a mismatch in stored injection parameters occurs.

16. In a system for infusing contrast media from a syringe reservoir through a catheter into a vascular system of a patient by means of a plunger acting against load conditions such as those dependent on plunger resistance, syringe reservoir volume, contrast media viscosity and catheter length and flow area, powered drive means operatively connected to the plunger for displacement thereof to effect infusion at a predetermined flow rate and pressure, servo means connected to said drive means for establishing said predetermined flow rate and pressure in accordance with a plurality of injection control parameters independent of said load conditions, means for selecting said injection control parameters pursuant to which the predetermined flow rate and pressure is established to controllably change the flow rates and pressures under which the contrast media is infused, memory means for storing sets of said injection control parameters, means for producing an identification tag for association with each set of said injection control parameters and for storing said tags with said sets in said memory means, recall means responsive to a given one of the tags for recalling from said memory means an associated set of the injection control parameters to enable quick recall of routine sets of the injection control parameters without operator input prior to infusion.

17. An angiographic injector device as recited in claim 16, further including means for verifying each of said recalled input parameters prior to an injection.

18. An angiographic injector device as recited in claim 17, wherein said means for verifying comprises redundant memories for storing each of said injection parameters, means for comparing the contents of said injection parameter stored in said redundant memories, and means for disabling said injector device or alerting the operator in the event of a difference in said comparison of data between said redundant memories.

19. The system of claim 16, wherein at least one of said sets of injector control parameters includes information for performing multi-phasic injection whereby predetermined portions of said contrast media are injected with predetermined ones of said injection control parameters until said infusion is complete.

20. The system of claim 19, wherein said at least one of said sets of injection control parameters includes information for performing said multi-phasic injection until said contrast media in said syringe reservoir is exhausted.

21. The system of claim 19, wherein said predetermined portions of said contrast media correspond to predetermined volumes of said contrast media.

22. The system of claim 19, wherein said predetermined portions of said contrast media correspond to injections of said contrast media for a predetermined duration.

23. The system of claim 16, and further including means for selecting one of a plurality of syringe size parameters, said syringe size parameter being used to calculate said predetermined flow rate and pressure in accordance with said plurality of injection control parameters.

24. The system of claim 23, wherein said syringe size parameter is used to control the displacement of said plunger, to determine the volume of contrast media remaining in said syringe reservoir, and to determine the volume of contrast media infused from said syringe reservoir.

25. In a system for infusing contrast media from a syringe reservoir through a catheter into a vascular system of a patient by means of a plunger acting against load conditions dependent on plunger resistance, syringe reservoir volume, contrast media viscosity and catheter length and flow area, powered drive means operatively connected to the plunger for displacement thereof to effect infusion at a predetermined flow rate and pressure, servo means connected to said drive means for establishing said predetermined flow rate and pressure in accordance with a plurality of injection control parameters independent of said load conditions, means for selecting said injection control parameters pursuant to which the predetermined flow rate and pressure is established to controllably change the flow rates and pressures under which the contrast media is infused, self-calibration means for producing a test command signal positioning said drive means at a test position, means for monitoring said drive means to detect the actual position thereof, means for comparing the test position with the actual position, and means for re-calibrating said drive means on the basis of said comparison.

26. In a system for infusing contrast media from a syringe reservoir through a catheter into a vascular system of a patient by means of a plunger acting against load conditions dependent on plunger resistance, syringe reservoir volume, contrast media viscosity and catheter length and flow area, powered drive means operatively connected to the plunger for displacement thereof to effect infusion at a predetermined flow rate and pressure, servo means connected to said drive means for establishing said predetermined flow rate and pressure in accordance with a plurality of injection control parameters independent of said load conditions, means for selecting said injection control parameters pursuant to which the predetermined flow rate and pressure is established to controllably change the flow rates and pressures under which the contrast media is infused, mechanical stop means engagable by the plunger for limiting displacement thereof to a limit position, controller means operatively connected to the mechanical stop means and the servo means for establishing the limit position in accordance with a selected one of the injection control parameters, and interlock means for alternatively enabling the drive means and the controller means to prevent said displacement of the plunger until said limit position is established through the controller means.

27. In a system for infusion of contrast media from a reservoir into a patient in response to discharge of the media from a port of the reservoir, including injection drive means for effecting said discharge of the media from the port, means for generating at least one injection control signal as a function of at least one injection parameter supplied thereto, means for monitoring at least one operational condition during said discharge of the media, servo control means operatively interconnecting the generating means, the monitoring means and the drive means for establishing said infusion of the media in accordance with said injection parameter under the monitored operational condition, said drive means including a media displacing piston and said monitored operational condition being the position of the piston, said servo control means including a stop member, a control motor operatively connected to the stop member, means for producing a stop command signal when the monitored position of the piston reaches a forward limit and means responsive to said stop command signal for actuating the control motor to advance the stop member whereby forward movement of the piston beyond said forward limit is mechanically prevented by the stop member.

28. In a system for infusing contrast media from a syringe reservoir through a catheter into a vascular system of a patient by means of a plunger acting against load conditions dependent on plunger resistance, syringe reservoir volume, contrast media viscosity and catheter length and flow area, powered drive means operatively connected to the plunger for displacement thereof to effect infusion at a predetermined flow rate and pressure, servo means connected to said drive means for establishing said predetermined flow rate and pressure in accordance with a plurality of injection control parameters independent of said load conditions, means for selecting said injection control parameters pursuant to which the predetermined flow rate and pressure is established to controllably change the flow rates and pressures under which the contrast media is infused, said injection control parameters being selected from a group including flow rate of the contrast media, volume of the contrast media, duration of infusion, pressure limit of said contrast media, x-ray photo delay, inject delay and flow rise/fall time of pressure of the contrast media, memory means for storing sets of said injection control parameters, means for producing an identification tag for association with each set of said injection parameters and for storing said tags with said sets in said memory means, recall means responsive to a given one of the tags for recalling from said memory means an associated set of the injection parameters to enable quick recall of routine sets of the injection parameters without operator input prior to infusion.

29. In a system for infusion of contrast media from a reservoir into a patient in response to discharge of the media from a port of the reservoir, including injection drive means for effecting said discharge of the media from the port, means for generating at least one injection control signal as a function of at least one injection parameter supplied thereto, means for monitoring at least one operational condition during said discharge of the media, servo control means operatively interconnecting the generating means, the monitoring means and the drive means for establishing said infusion of the media in accordance with said injection parameter under the monitored operational condition, memory means for storing sets of said injection control parameters, means for producing an identification tag for association with each set of said injection parameters and for storing said tags with said sets in said memory means, recall means responsive to a given one of the tags for recalling from said memory means an associated set of the injection parameters to enable quick recall of routine sets of the injection parameters without operator input prior to infusion.

30. The system of claim 29, and further including a plunger, and powered drive means operatively connected to said plunger for effecting infusion of said contrast media at a predetermined flow rate and pressure, said servo control means connected to said powered drive means for establishing said predetermined flow rate and pressure in accordance with said at least one injection parameter.

31. The system of claim 30, and further including a mechanical stop means engagable by the plunger for limiting displacement thereof to a limit position and controller means operatively connected to said mechanical stop means and the servo control means for establishing the limit position in accordance with a selected one of said at least one injection control parameter.

32. The system of claim 29, wherein at least one of said sets of injection control parameters includes information for performing multi-phasic injection whereby predetermined portions of said contrast media are injected with predetermined ones of said injection contorl parameters until said infusion is complete.

33. The system of claim 32, wherein said at least one of said sets of injection control parameters includes information for performing said multi-phasic injection until said contrast media in said syringe reservoir is exhausted.

34. The system of claim 32, wherein said predetermined portions of said contrast media correspond to predetermined volumes of said contrast media.

35. The system of claim 32, wherein said predetermined portions of said contrast media correspond to injections of said contrast media for a predetermined duration.

36. The system of claim 29, and further including means for selecting one of a plurality of syringe size parameters, said syringe size parameter being used to calculate said predetermined flow rate and pressure in accordance with said plurality of injection control parameters.

37. The system of claim 36, wherein said syringe size parameter is used to control the displacement of said plunger, to determine the volume of contrast media remaining in said syringe reservoir, and to determine the volume of contrast media infused from said syringe reservoir.

* * * * *